(12) United States Patent
Anki et al.

(10) Patent No.: US 12,156,637 B2
(45) Date of Patent: Dec. 3, 2024

(54) CLEANING DEVICE FOR SURGICAL TOOL

(71) Applicant: Gulf Medical Technologies, Kuwait (KW)

(72) Inventors: Ahmad Nabeel Anki, Kuwait (KW); Salman Khalifah Al Sabah, Kuwait (KW)

(73) Assignee: Gulf Medical Technologies, Kuwait (KW)

( * ) Notice: Subject to any disclaimer, the term of this patent is extended or adjusted under 35 U.S.C. 154(b) by 0 days.

(21) Appl. No.: 17/448,189

(22) Filed: Sep. 20, 2021

(65) Prior Publication Data

US 2022/0249197 A1 Aug. 11, 2022

Related U.S. Application Data

(63) Continuation of application No. 17/089,676, filed on Nov. 4, 2020, now Pat. No. 11,123,152.

(Continued)

(51) Int. Cl.
*A61B 1/00* (2006.01)
*A61B 90/70* (2016.01)
(Continued)

(52) U.S. Cl.
CPC ...... *A61B 1/00135* (2013.01); *A61B 1/00042* (2022.02); *A61B 90/70* (2016.02); *A61L 2/18* (2013.01); *A61L 2/20* (2013.01); *A61B 1/00009* (2013.01); *A61L 2202/14* (2013.01); *A61L 2202/15* (2013.01); *A61L 2202/17* (2013.01); *A61L 2202/24* (2013.01)

(58) Field of Classification Search
None
See application file for complete search history.

(56) References Cited

U.S. PATENT DOCUMENTS

| 5,647,840 A | 7/1997 | Amelio et al. |
|---|---|---|
| 6,126,592 A | 10/2000 | Proch et al. |

(Continued)

FOREIGN PATENT DOCUMENTS

| JP | 2010/184023 A | 8/2010 |
|---|---|---|
| KR | 10-1771541 B1 | 2/2016 |

OTHER PUBLICATIONS

International Search Report for corresponding International Application No. PCT/IB2020/060396, mailed on Mar. 31, 2021, 6 pages.

(Continued)

*Primary Examiner* — Rita P Adhlakha
(74) *Attorney, Agent, or Firm* — Winthrop & Weinstine, P.A.

(57) ABSTRACT

The present disclosure relates to a cleaning device system for a surgical tool. Particularly, the present disclosure relates to a novel and advantageous cleaning device system for a laparoscope. The cleaning device system includes a cleaning device, a module, and a control pad. The cleaning device includes a shaft and a nozzle for directing irrigation fluid and drying fluid towards an end of the surgical tool. The module may be a self-contained unit holding saline for cleaning, $CO_2$ for drying, and a battery for powering the system. The cleaning device may be a retrofit device for an existing laparoscope or may be incorporated into a new laparoscope.

13 Claims, 45 Drawing Sheets

Related U.S. Application Data

(60) Provisional application No. 62/929,955, filed on Nov. 4, 2019.

(51) Int. Cl.
*A61L 2/18* (2006.01)
*A61L 2/20* (2006.01)

(56) References Cited

U.S. PATENT DOCUMENTS

| | | |
|---|---|---|
| 8,460,180 B1 | 6/2013 | Zarate et al. |
| 8,535,220 B2 | 9/2013 | Mondschein |
| 8,721,529 B2 | 5/2014 | Hess et al. |
| 9,913,576 B2 | 3/2018 | Ray et al. |
| 2007/0049794 A1 | 3/2007 | Glassenberg et al. |
| 2008/0081648 A1 | 4/2008 | Kang et al. |
| 2008/0081948 A1 | 4/2008 | Weisenburgh et al. |
| 2008/0200765 A1* | 8/2008 | Mondschein ........ A61B 1/3132 600/157 |
| 2015/0265138 A1* | 9/2015 | Poll .................... A61B 1/00119 600/123 |
| 2015/0282695 A1 | 10/2015 | Tay et al. |
| 2018/0116496 A1 | 5/2018 | Arcot et al. |
| 2018/0214016 A1 | 8/2018 | Thommen et al. |
| 2018/0318459 A1* | 11/2018 | Hancock ............... A61L 2/0029 |

OTHER PUBLICATIONS

Invitation to Pay Additional Fees for corresponding International Application No. PCT/IB2020/060396, mailed on Feb. 8, 2021, 8 pages.

Office Action in corresponding Saudi Arabian Appln. No. 522432519, dated Aug. 7, 2023, 10 pages (with English translation).

Written Opinion for corresponding International Application No. PCT/IB2020/060396, mailed on Mar. 31, 2021, 7 pages.

Office Action in Kuwaiti Application No. KW/P/2022/000534, mailed on Mar. 10, 2024, 9 pages.

* cited by examiner

Soiled Scope

After Initial Wash
5psi-Irrigation
40psi-Jet-Dry

Pre-Soiled Scope

Soiled Scope

Post Cleaning Scope

CLEANING DEVICE FOR SURGICAL TOOL

CROSS-REFERENCE TO RELATED APPLICATIONS

The present application is a Continuation of U.S. application Ser. No. 17/089,676, filed Nov. 4, 2020, which claims the benefit of U.S. Provisional Application No. 62/929,955 filed Nov. 4, 2019, the contents of which are hereby fully incorporated herein by reference.

FIELD OF THE INVENTION

The present disclosure relates to a cleaning device system for a surgical tool. Particularly, the present disclosure relates to a novel and advantageous cleaning device system for a laparoscope. The cleaning device system includes a cleaning device, a module, and a control pad. The cleaning device includes a shaft and a nozzle for directing irrigation fluid and drying fluid towards an end of the surgical tool. The module may be a self-contained unit holding saline for cleaning, $CO_2$ for drying, and a battery for powering the system. The cleaning device may be a retrofit device for an existing laparoscope or may be incorporated into a new laparoscope.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Laparoscope use provides a means for visual guidance during procedures that is low-risk and minimally invasive. During a procedure it is common for the laparoscope lens to become occluded with various bodily fluids such as fatty fluids and blood, as well as by fog. Presently, the common procedure used to clean the lens requires removing the lens from the body, resulting in procedural delay and increased opportunity for infection. An average procedure requires a lens cleaning rate of approximately 6 cleaning events per hour.

Thus, there is a need in the art for a device for cleaning a laparoscope lens, and other in vivo lenses, that does not require removal of the lens from the body.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure relates to a cleaning device for a surgical tool. Particularly, the present disclosure relates to a novel and advantageous self-contained cleaning device system for in vivo cleaning of a lens of a surgical tool, such as a laparoscope. The cleaning device system may be used to a retrofit an existing surgical tool or may be incorporated into a new surgical tool.

The cleaning device system may be provided as a laparoscope accessory that may be used during surgical procedures, such as in the abdomen. The system may be self-contained without requiring wiring or hook up to operating room resources. More specifically, the cleaning device system may be a self-contained, battery powered self-cleaning retrofit kit, including built-in heating, irrigation, and jet dry or suction systems. The system allows for lens cleaning without requiring removal of the laparoscope lens from the body, thus improving procedure time and workflow. In some embodiments, the cleaning device fits onto a laparoscope and provides a flow of fluid across the laparoscope lens.

The present disclosure, in one or more embodiments, additionally relates to a cleaning device system for use with a surgical device having a shaft and a lens at a distal end of the shaft is provided for cleaning the lens. The cleaning device system may be a self-contained, battery powered self-cleaning retrofit kit, including built-in heating, irrigation, and drying systems. In one embodiment, the cleaning device system comprises a cleaning device, a module, and a control pad. The control pad may be provided as part of the cleaning device or separate from and operatively connected to the cleaning device. The cleaning device comprises a sheath and a nozzle. The sheath is configured for fitting over the shaft of the surgical device and has an irrigation channel, a drying channel, and a heating channel. The heating channel is disposed proximate the irrigation channel and may be used to warm a first fluid. The nozzle is coupled to a distal end of the sheath. The nozzle has an irrigation port and a drying port, the irrigation channel terminating at the irrigation port and the drying channel terminating at the drying port. The module houses an irrigation fluid reservoir, a gas canister, and a power source. A first fluid is dispensed from the irrigation fluid reservoir in the module through the irrigation channel in the sheath and out the irrigation port in the nozzle. A second fluid is dispensed from the gas canister in the module through the drying channel in the shaft and out the drying port in the nozzle. The control pad may have a first button and a second button, wherein the first button runs a cleaning cycle including dispensing the first fluid and the second button runs a drying cycle including dispensing the second fluid. In some embodiments, the cleaning cycle may further comprise dispensing the second fluid.

In a further embodiment, a cleaning device system for use with a surgical device having a shaft and a lens at a distal end of the shaft is provided for cleaning the lens using a non-tactile mechanism for activating a cleaning cycle. The cleaning device comprises a shaft, a nozzle, a module, and a non-tactile mechanism for activating a cleaning cycle. The sheath is configured for fitting over the shaft of the surgical device and has an irrigation channel and a drying channel. The nozzle is coupled to a distal end of the sheath. The nozzle has an irrigation port and a drying port, the irrigation channel terminating at the irrigation port and the drying channel terminating at the drying port. The module houses an irrigation fluid reservoir, a gas canister, and a power source. A first fluid is dispensed from the irrigation fluid reservoir in the module through the irrigation channel in the sheath and out the irrigation port in the nozzle. A second fluid is dispensed from the gas canister in the module through the drying channel in the shaft and out the drying port in the nozzle. In some embodiments, the non-tactile mechanism may be autonomous. Such autonomous mechanism may be comprise a sensor that senses when the lens is dirty by evaluating images from the lens or a sensor that senses when the lens is dirty by evaluating light reflection. In another embodiment, the non-tactile mechanism is voice activation. In some embodiments, the non-tactile mechanism may activate a drying cycle. A further mechanism, tactile or non-tactile, may also be provided to activate a supplemental cleaning cycle or drying cycle.

A cleaning device system for use with a surgical device having a shaft and a lens at a distal end of the shaft is provided in yet a further embodiment. The cleaning device system comprises a cleaning device, a module, and a control pad. The control pad may be provide as part of the cleaning device or separate from and operatively connected to the cleaning device. The cleaning device may comprise a sheath and a nozzle. The sheath may be for fitting over the shaft of the surgical device, the sheath. The sheath may have an irrigation channel, a drying channel, and a heating channel, wherein the heating channel is disposed proximate the irrigation channel. The nozzle may be coupled to a distal end of the sheath. The nozzle may have an irrigation port and a drying port, the irrigation channel terminating at the irrigation port and the drying channel terminating at the drying port. The module may house an irrigation fluid reservoir, a $CO_2$ canister, and a power source. The irrigation fluid reservoir may have a volume sufficient for at least ten cleanings without refilling. Saline is dispensed from the irrigation fluid reservoir in the module through the irrigation channel in the sheath and out the irrigation port in the nozzle and $CO_2$ gas is dispensed from the gas canister in the module through the drying channel in the shaft and out the drying port in the nozzle. The saline is heated to a temperature of at least 104° F. in the irrigation channel. The control pad may have a first button and a second button, wherein the first button runs a cleaning cycle comprising dispensing the saline and dispensing the $CO_2$ and the second button runs a supplemental drying cycle comprising dispensing the $CO_2$.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 3b illustrates the control pad of FIG. 3a.

FIG. 3c illustrates a further view of the control pad of FIG. 3a.

FIG. 4b illustrates a further view of the a module/control box of FIG. 4a.

FIG. 7b illustrate an end view of the sheath of FIG. 7a.

FIG. 7c illustrate an end view of the sheath of FIG. 7a.

FIG. 8b illustrates an end view of the sheath of FIG. 8a.

FIG. 16c illustrates an end view of the injection molded tip of FIG. 16a.

FIG. 19b illustrates the sheath of FIG. 19a.

FIG. 19c illustrates the sheath of FIG. 19a.

DETAILED DESCRIPTION

Figure 1A:
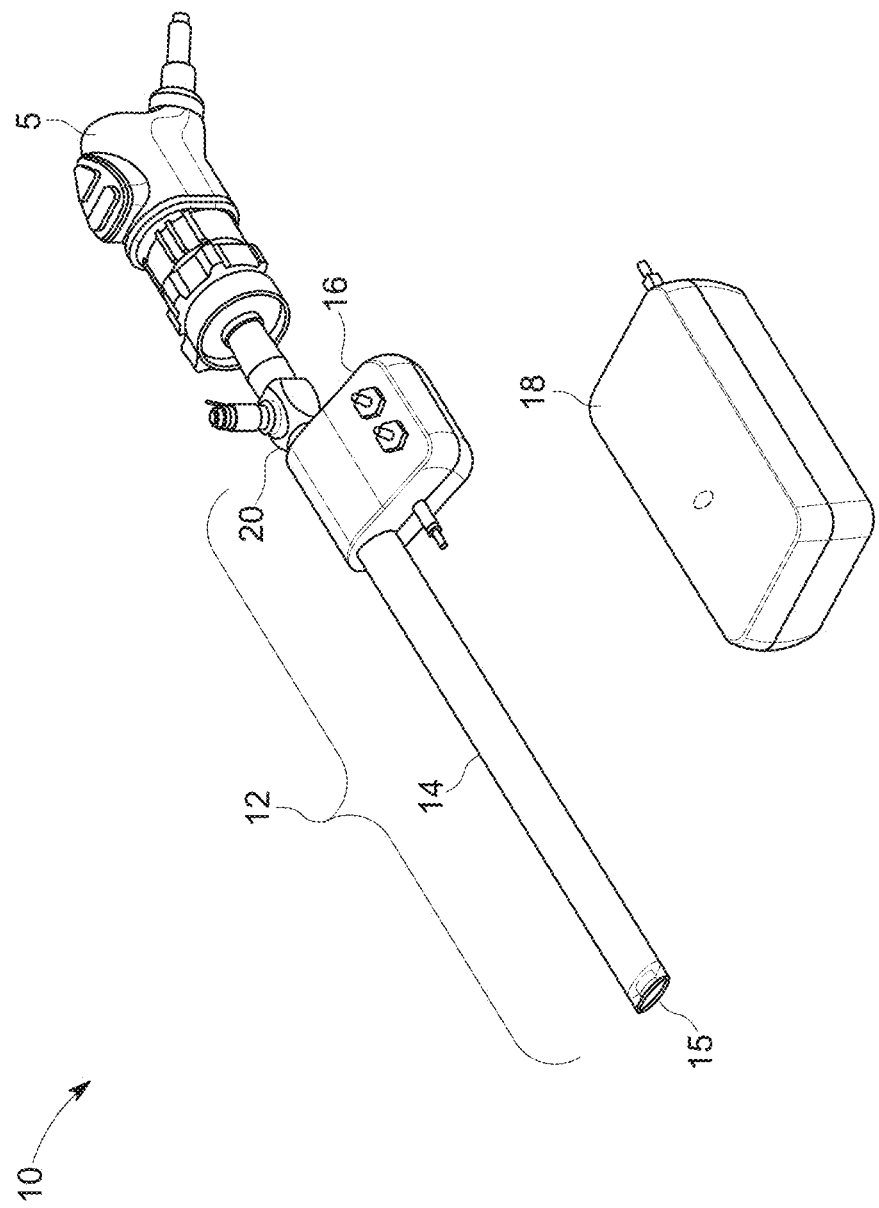
FIG. 1a illustrates a cleaning device mounted on a laparoscope, in accordance with one embodiment.

The present disclosure relates to a cleaning device system for a surgical tool. Particularly, the present disclosure relates to a novel and advantageous cleaning device system for a laparoscope. The cleaning device system includes a cleaning device, a module, and a control pad. The cleaning device includes a shaft and a nozzle for directing irrigation fluid and drying fluid towards an end of the surgical tool. The module may be a self-contained unit holding saline for cleaning, $CO_2$ for drying, and a battery for powering the system. The cleaning device may be a retrofit device for an existing laparoscope or may be incorporated into a new laparoscope or similar device. For example, in some embodiments, an inventive laparoscope or other scope may include one or more of the design elements of the present invention in a manner that is integrated within the shaft of the scope, and such that no additional accessories are required to utilize the functionality described herein.

The cleaning device system may be provided as a laparoscope accessory that may be used during surgical procedures, such as in the abdomen. The system may be self-contained without requiring wiring or hook up to operating room resources. More specifically, the cleaning device system may be a self-contained, battery powered self-cleaning retrofit kit, including built-in heating, irrigation, and jet dry or suction systems. The system allows for lens cleaning without requiring removal of the laparoscope lens from the body, thus improving procedure time and workflow. In some embodiments, the cleaning device fits onto a laparoscope and provides a flow of fluid across the laparoscope lens. The volume of fluid remaining in the body may be kept low in order to ensure absorption following the procedure.

In general, the cleaning device may be used with any surgical instrument that is used in vivo and includes a shaft with an end that requires cleaning. The cleaning device system may be used to clear, for example, fatty fluids, blood, and fog from a lens of a surgical device, such as a laparoscope, while the surgical device is in vivo.

In one embodiment, the cleaning device fits onto a laparoscope and works by providing a controlled flow of a first fluid, such as water or saline, across the lens followed by a blast of $CO_2$ or other fluid to aid in clearing loosed debris and the first fluid and to dry the lens. The first fluid, e.g. water or saline, the second fluid, e.g. $CO_2$, and power, e.g. a battery, may be provided in the cleaning device system such that no hook up to operating room resources is necessary. The volume of fluid remaining in the body after cleaning may be minimized to facilitate absorption following the procedure.

It is to be appreciated that the cleaning device may alternatively be designed to attach to surgical robots or other devices by customizing dimensions of a sheath of the cleaning device, and work to clean such lenses of any in vivo device in substantially the same manner as described herein with respect to laparoscopes. The cleaning device may be configured to facilitate articulation such that it may be used with surgical devices that articulate. Further, the cleaning device may be configured to be flexible (such as having a flexible sheath) for use with endoscopy type systems.

In some embodiments, the system may be configured for abdominal insufflation. This comprises pumping a gas, for example $CO_2$, into the peritoneal cavity producing a pneumoperitoneum to cause an increase in intra-abdominal pressure (TAP). In order to perform such insufflation, the cleaning device may be activated to dispense only $CO_2$, without irrigating. For insufflation, a sheath having a drying tube sized for appropriate $CO_2$ flow and a nozzle configured to direct $CO_2$ outwardly from the device. Carbon dioxide may insufflated into the peritoneal cavity at a rate of 4-6 liter $min^{-1}$ to a pressure of 10-20 mm Hg.

Figure 1B:
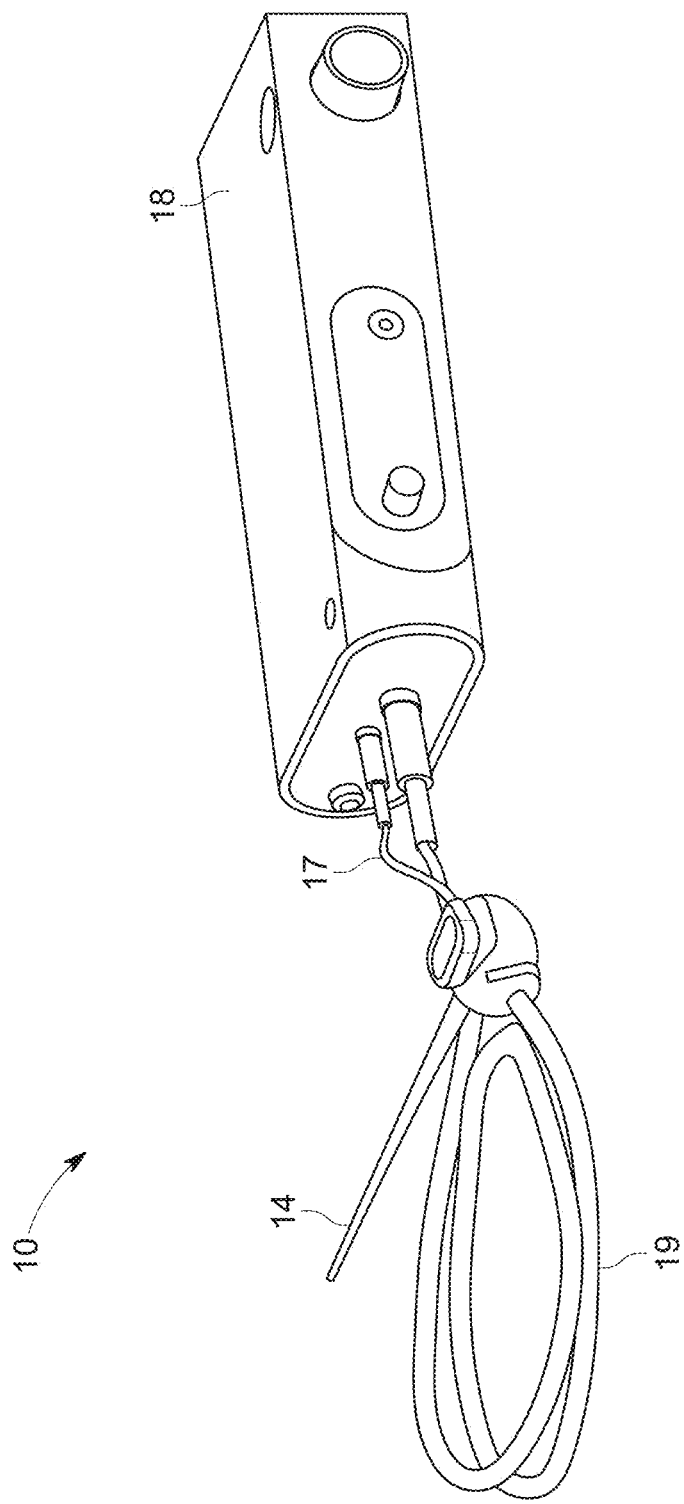
FIG. 1b illustrates a cleaning device system, in accordance with another embodiment.

FIGS. 1a and 1b illustrate embodiments of a cleaning device system. FIG. 1a illustrates the cleaning device system 10 with a cleaning device 12 thereof mounted to a laparoscope 5. FIG. 1b illustrates the cleaning device system unassociated with a surgical device. As shown, the cleaning device system 10 may include a cleaning device 12 and a module or control box 18. The cleaning device 12 comprises a sheath (also referred to as a shaft) 14, a nozzle 15, a control pad 16, and a retaining feature 20. In the embodiment shown in FIGS. 1a and 1b, the module 18 carries a reservoir for holding fluid for cleaning the lens and receives a $CO_2$ canister or cartridge for drying the lens. While a $CO_2$ canister is discussed herein, any suitable material or method for jet drying may be used in such embodiments. The module 18 may further include a battery for powering the cleaning device system. As shown in FIG. 1b, tubing 17 may extend between the cleaning device 12 and the module 18 to feed first and second fluids, such as saline and $CO_2$, from the module 18 to the cleaning device 12. Cable 19 runs from the module 18 to the control pad 16 to power the control pad 16. A transportation box (shown in FIGS. 5a and 5b) may also be provided.

As shown in FIG. 1a, the cleaning device 12 may be mounted to an existing laparoscope such that, as deployed, the lens of the laparoscope is exposed and a user may operate the laparoscope to use the laparoscope as normal and actuate buttons on the control pad of the cleaning device to clean the lens of the laparoscope. The control pad may be used to dispel a first fluid, such as saline or water, across the lens to remove debris from the lens and blow a second fluid, such as $CO_2$, across the lens to further remove debris dry the lens. The present disclosure specifically discusses the cleaning device as used with 10 mm 30 degree laparoscopes. Such specificity is for illustrative purposes only and is not intended to be limiting. With specific reference to laparoscopes, the cleaning device may be used with virtually any size of sheath such as 3 mm, 5 mm, 8 mm, 10 mm diameter and 0 degree, 10 degree, 30 degree, and 45 degree angles. It is to be appreciated that the length and diameter of the sheath may be customized for the surgical device or surgical robot with which it is to be used.

The cleaning device system may be used to irrigate and dry the lens at the end of a surgical device, such as a laparoscope, or a surgical robot. In various embodiments, drying may be done by jet-drying or by suction. In some embodiments, cleaning may be a closed loop. The cleaning device system may be a self-contained system that carries its own irrigation fluid, drying mechanism, and battery such that operating room water, air, and electricity are not required. In other embodiments, the cleaning device system may have connections to operating room water, air, and/or electricity. Further, when provided as a self-contained system, the cleaning device system may nevertheless have back up connections to operating room water, air, and/or electricity.

In some embodiments, all or part of the cleaning device system may be disposable. For example, in one embodiment, the sheath and control pad/grip portions are each disposable, while the control pad and module may be reusable. In another embodiment, only the sheath is disposable, while the other elements are reusable. In embodiments utilizing a $CO_2$ canister, the canister may be disposable. Likewise, the reservoir may be either fully replaceable or reusable. In general, it may be useful for at least heater elements and electronics to be reusable. In alternative embodiments, the cleaning device system may be fully disposable.

Figure 2A:
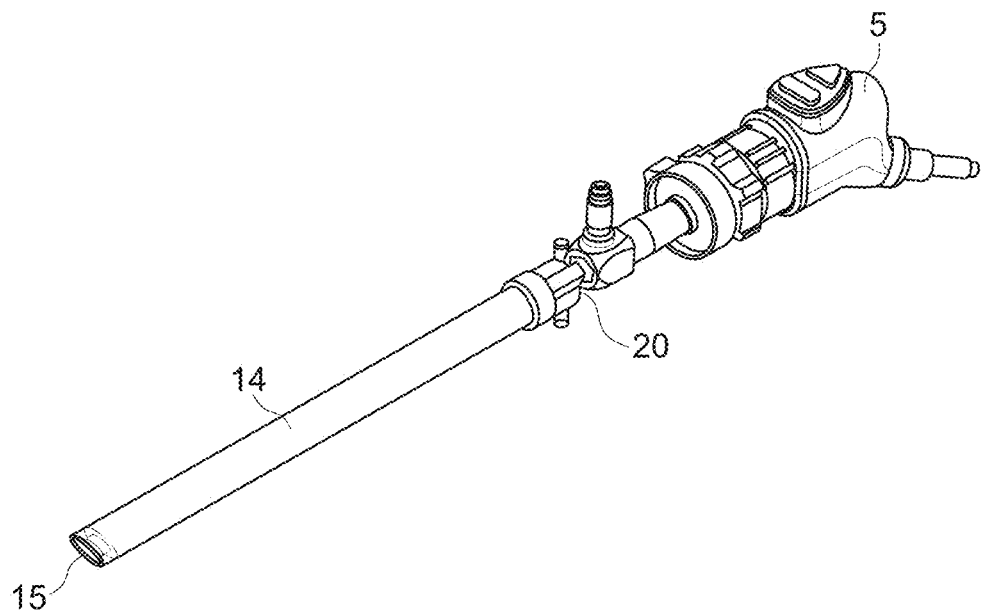
FIG. 2a illustrates a cleaning device mounted on a laparoscope, in accordance with one embodiment.
Figure 2B:
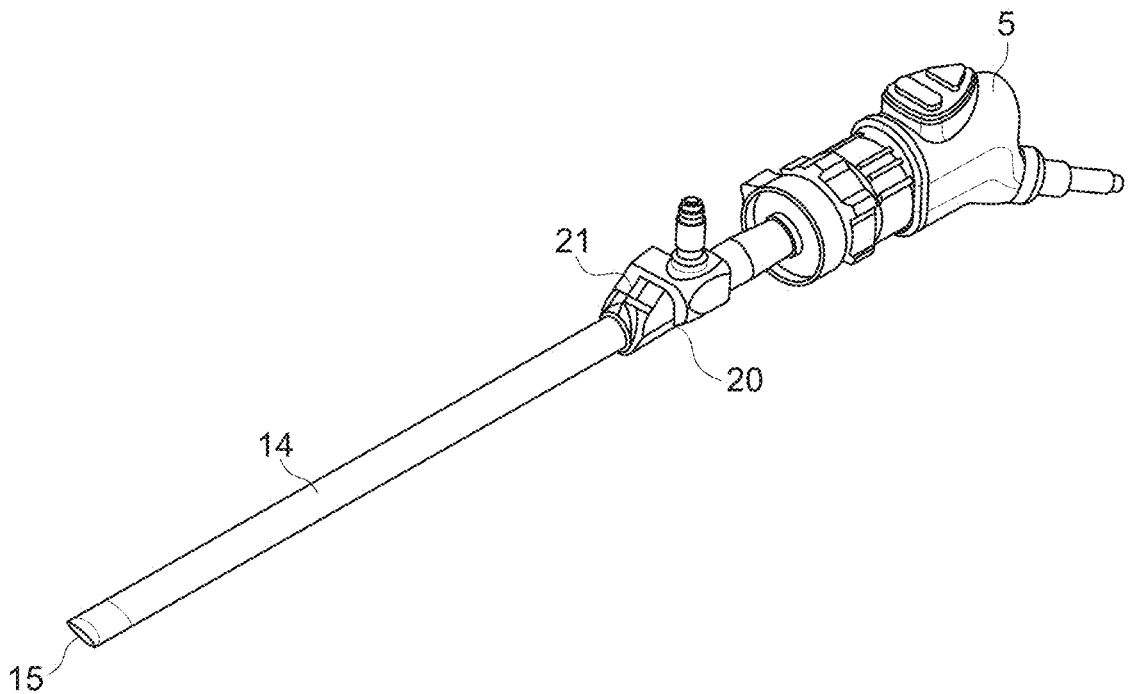
FIG. 2b illustrates a cleaning device mounted on a laparoscope, in accordance with another embodiment.
Figure 2C:
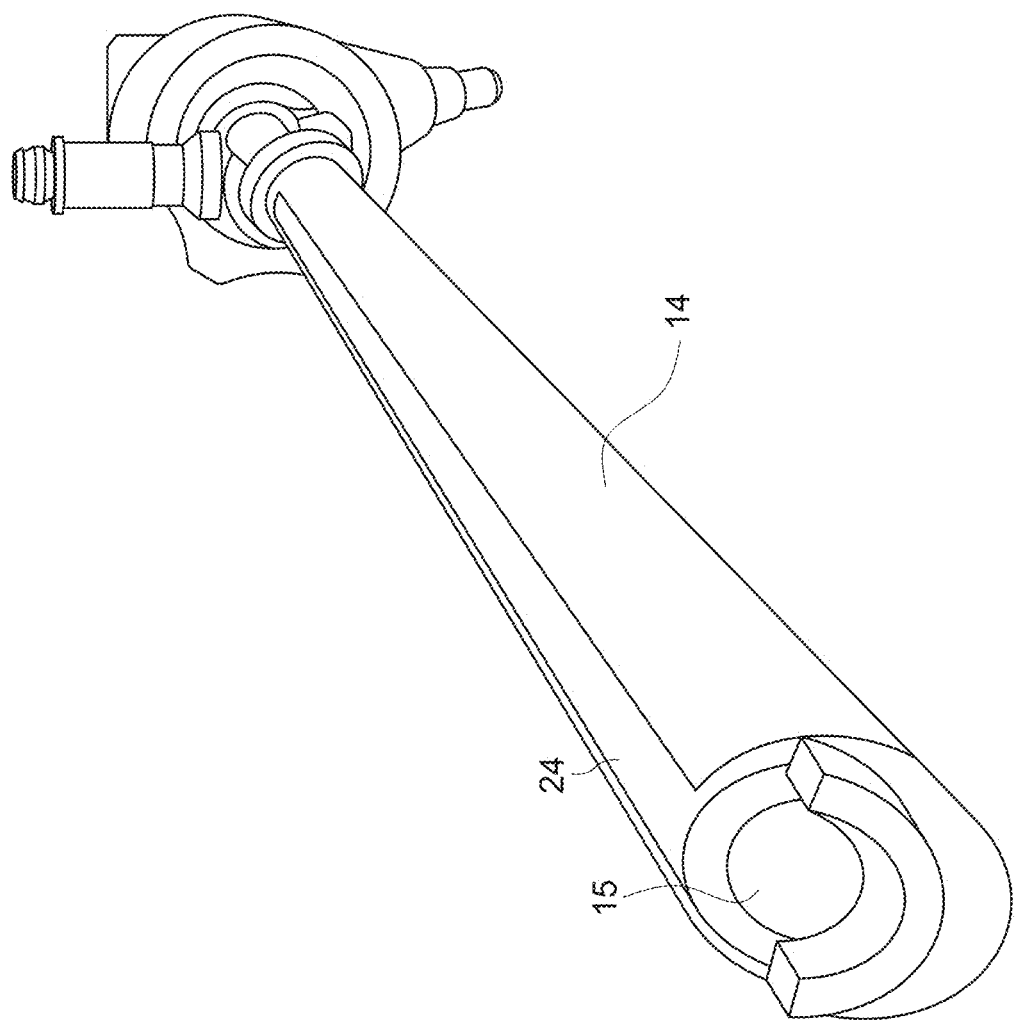
FIG. 2c illustrates a cleaning device mounted on a laparoscope, in accordance with yet another embodiment.

FIGS. 2a, 2b, and 2c illustrate various embodiments of a sheath 14 and nozzle 15 of a cleaning device mounted on a laparoscope 5 in accordance with other embodiments. The sheath may have a retaining feature 20 for restraining the sheath 14 on the surgical device. FIG. 2b further illustrates the shaft tube set receptors 21 for receiving tubing from the module. In the embodiment of FIG. 2c, the sheath 14 is c-shaped and has an open channel 24 along an upper surface.

FIG. 2c further illustrates one embodiment of a nozzle 15. The nozzle is provided at the distal end of the sheath and may connect to a tip of the sheath. The nozzle may be configured to direct irrigation fluid and $CO_2$ (or other fluid or suction) towards the lens.

Figure 3A:
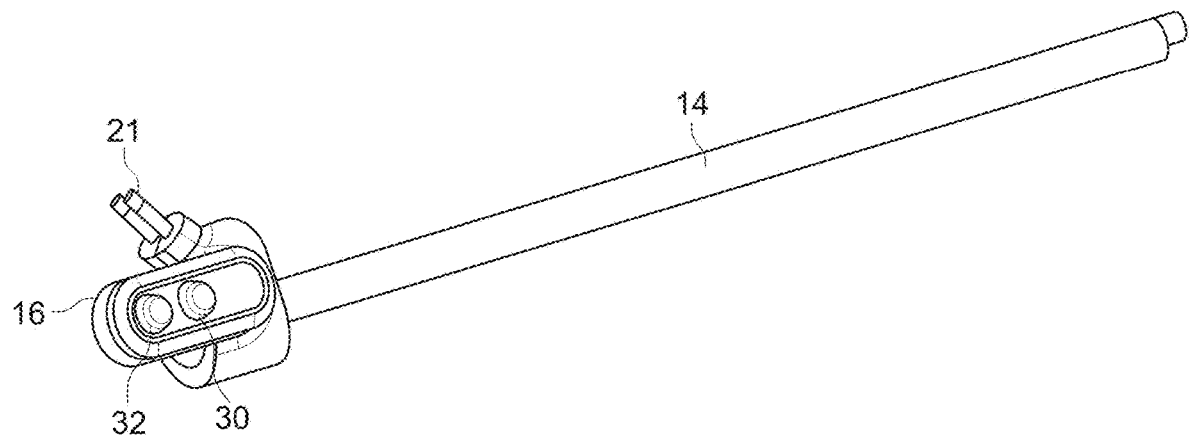
FIG. 3a illustrates a sheath of a cleaning device as coupled to a control pad, in accordance with one embodiment.
Figure 3B:
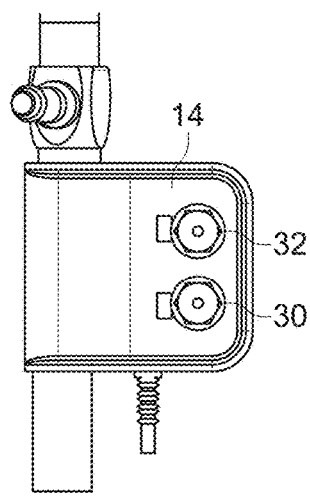
Figure 3C:
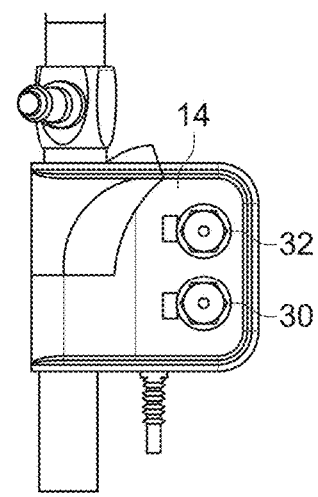

FIG. 3a illustrates the sheath 14 of a cleaning device as coupled to the control pad 16. FIGS. 3b and 3c illustrate the control pad 16, in accordance with various embodiments. The control pad may include a connection interface for connecting to the laparoscope distal to the light port of the laparoscope. As shown, the control pad includes interface controls—a first button 30 and a second button 32. The buttons may be provided, for example, on a two button membrane switch. The first button 30 may be referred to as an irrigation button and the second button 32 may be referred to as a drying button. The irrigation button 30 actuates an irrigation valve and the drying button 32 actuates a drying valve. In some embodiments, the first button 30 may actuate both the irrigation valve and the drying valve, thus launching a cleaning cycle, and the drying button 32 may have a supplemental drying function. In such embodiment, the irrigation button may be referred to as a cycle button, activating both flushing and drying functions. If the lens is not sufficiently dry after actuation of the cycle button 30, the drying button 32 may be actuated to trigger further drying.

The control pad is communicatively coupled to the module such that actuation of buttons on the control pad actuate valves in the module. For example, a cable may be provided between the control pad and the module. Alternatively, communication may be done via infrared, radio frequency, Bluetooth, or other.

The valves in the module may be mechanical valves or electrical valves. The buttons 30, 32 may actuate momentary switches such that the user controls the time of irrigation and/or drying. Alternatively, the buttons 30, 32 may actuate electric switches with a preset run time. In one embodiment, the valves are electronically controlled comprising buttons on the control pad and solenoid valves in the module. In an alternative embodiment, the interface controls may be provided on the module and a control pad may not be provided on the cleaning device.

While specific detail is given regarding one or more buttons being used to control irrigating and drying, this functionality by be otherwise triggered. For example, the cleaning device system may be provided with voice activation for controlling irrigating and drying. In another embodiment, cleaning may be automatic. More specifically, the cleaning device may detect when the lens of the surgical device is dirty and may run itself through one or more cleaning cycles. This may be done, for example, by using a light sensor and detecting refraction of light through the lens. In some embodiments, white light spectroscopy and software analysis of light reflection may be used to detect whether the lens is dirty. In another automatic embodiment, the cleaning device may detect that the lens is dirty by looking at the image generated by the camera and detecting that the image is blurry. In some embodiments, the cleaning device system may have an automatic run cycle capability but also have supplemental clean cycle or drying functionality via a control pad.

Figure 4A:
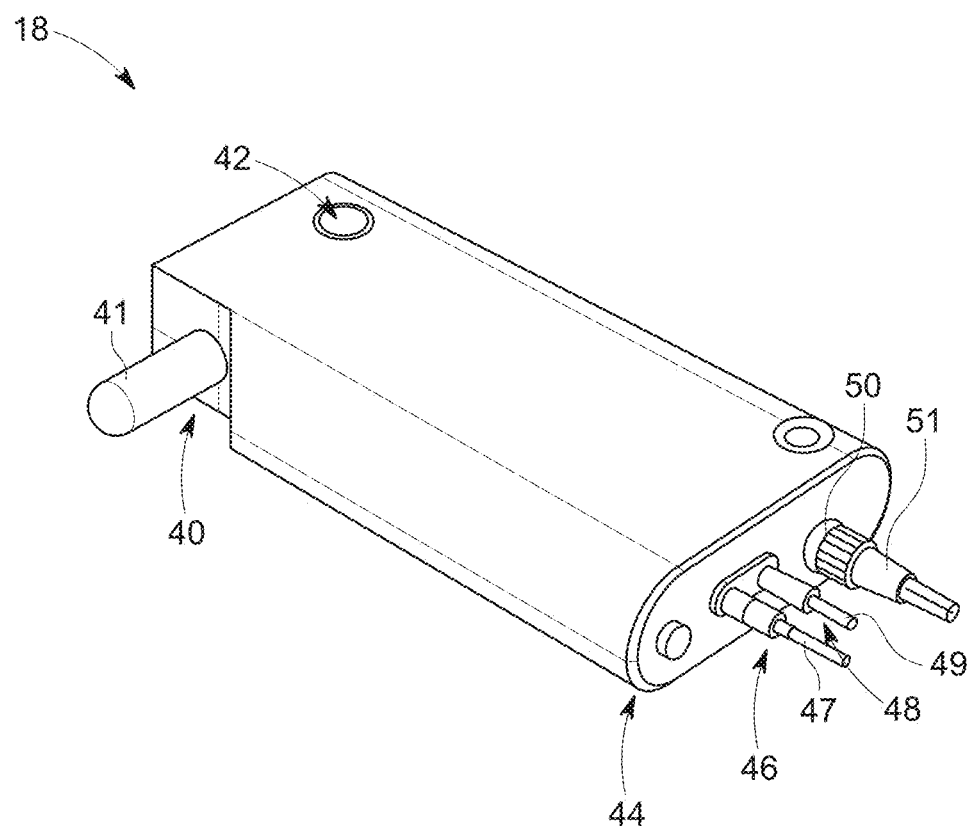
FIG. 4a illustrates a module/control box, in accordance with one embodiment.
Figure 4B:
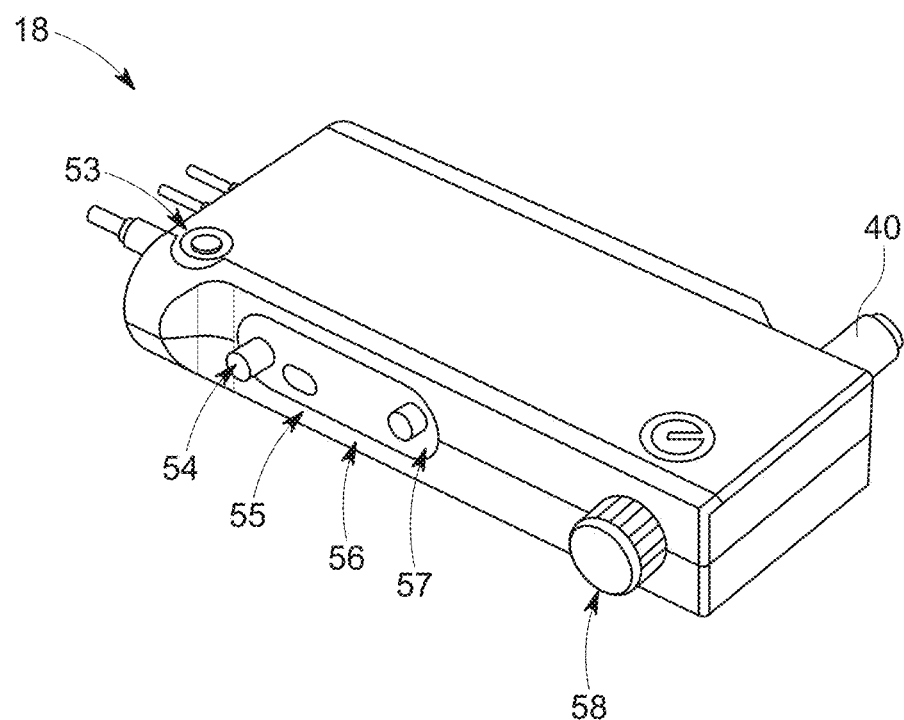

FIGS. 4*a* and 4*b* illustrate a module/control box 18 in accordance with one embodiment. The module 18 encloses a plurality of components of the cleaning device system. In general, the module is protective and has a small size. The module houses an irrigation fluid reservoir and $CO_2$ canister or cartridge. Each of the fluid reservoir and the $CO_2$ canister may be replaceable and/or refillable, including during a surgical procedure. The module may further house a battery. Alternatively the module may be configured to plug into operating room electricity. The $CO_2$ may be used to drive operation of each cleaning event, pumping the irrigation fluid and providing for air expulsion or vacuum. The fluid reservoir may be provided as a cartridge having capability of irrigation and waste storage and may be disposable. The $CO_2$ canister, fluid reservoir cartridge, and battery all may be replaceable mid-procedure as necessary. That being said, the fluid reservoir and/or the $CO_2$ canisters may have sufficient capacity such that it is not necessary to refill the fluid reservoir or replace the $CO_2$ canister during a procedure. In alternative embodiments, one or more of the fluid reservoir, $CO_2$ canister, or battery may not be provided in the module.

In one embodiment, the fluid reservoir is refillable and holds a volume sufficient to deliver, for example, between 8 and 20 cleaning cycles before needing to be refilled. In one embodiment, the fluid reservoir holds a volume sufficient to delivery 10 cleaning cycles before needing to be refilled. In one embodiment, the amount of fluid used per cleaning is 1.25 ml and the fluid reservoir holds a minimum of 30 ml of fluid plus an additional volume to accommodate system purge plus tolerance (10 ml). The volume of the fluid reservoir may be customized based on the intended use of the cleaning device system. In one embodiment, a 16 g compressed $CO_2$ cartridge is provided.

In one embodiment, the module may be sized to accommodate a fluid reservoir, $CO_2$ canister, and battery capable of between 5 and 20 cleanings with the cleanings having irrigation volumes ranging from about 0.25 mL to about 0.5 mL (for example, 1.25 or 1.5 mL) and irrigation times ranging from about 1 to about 3 seconds. For example, in one embodiment, the module may be sized to accommodate a fluid reservoir, $CO_2$ canister, and battery capable of 10 cleanings each having an irrigation of about 3 seconds. The fluid reservoir may have a size between about 10 mL and about 30 mL. In one embodiment, the amount of fluid used per cleaning is 1.25 ml and fluid dispensing is done at a minimum rate of 6 times per hour. The battery may have any suitable capacity. In one embodiment, the battery may have a 9.18 watt hour capacity.

FIG. 4*a* illustrates the module 18 having a $CO_2$ canister 40 received by a $CO_2$ port 41, pressure gauge 42, fill port 44, saline port 46, $CO_2$ port 48, and electrical connection port 50. The saline port 46 and $CO_2$ 48 port receive tube connectors 47 and 49 respectively. The tube connectors 47 and 49 receive tubing to connect to cleaning device. In alternative embodiments, the ports 46 and 48 may connect directly to the tubing. The electrical connection port 50 receives an electrical cable 51.

FIG. 4*b* illustrates the module 18 having a prime button 53, thermal adjustment knob 54, programming entry 55 (plugged), power switch 56, power entry 57, and pressure adjustment knob 58.

The module 18 may further house an electronics controller, a momentary switch for performing a system purge, a power switch to power on the system, and a regulator. The momentary switch for performing a system purge may be incorporated into a power-up sequence, i.e., the device is plugged in, the power switch is pressed, powering on unit followed by a volume of fluid being dispensed through the system.

Figure 5A:
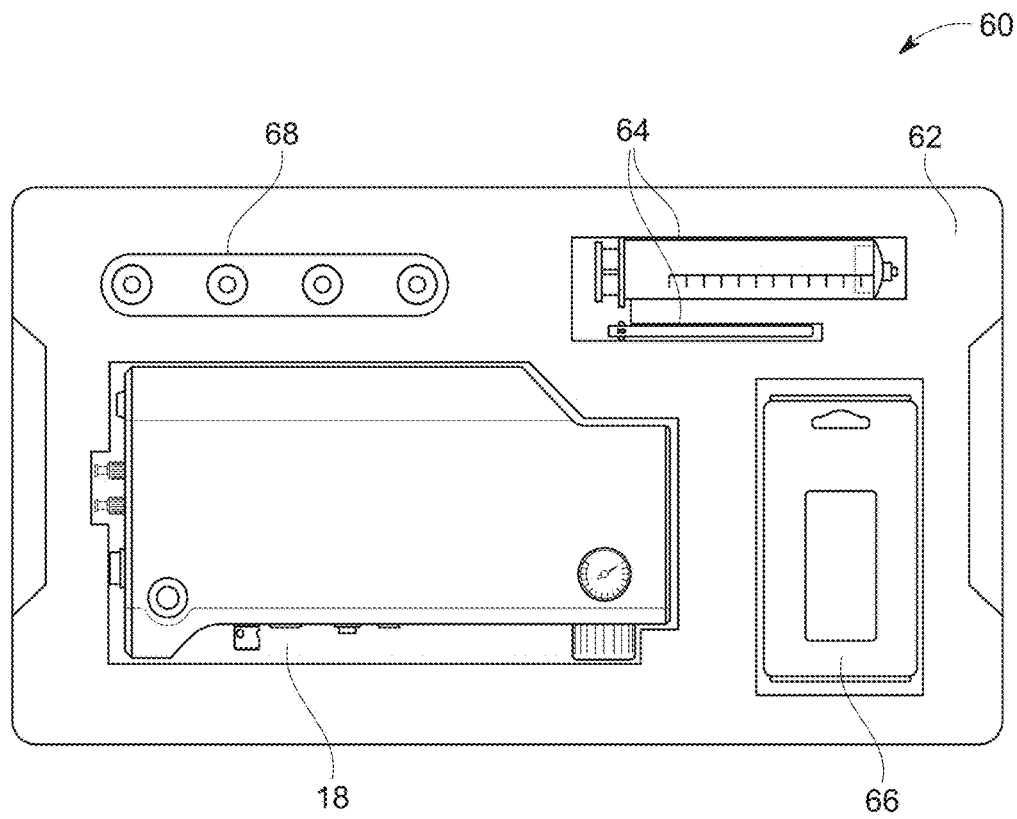
FIG. 5a illustrates a top tray of a transportation box, in accordance with one embodiment.
Figure 5B:
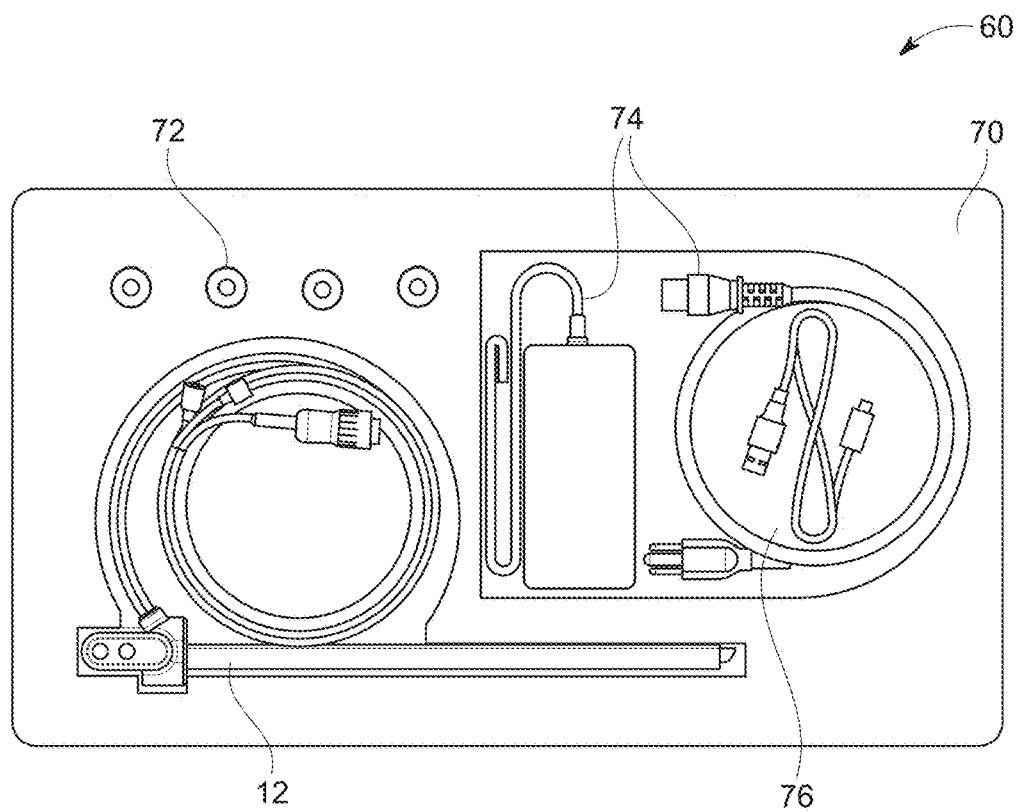
FIG. 5b illustrates a bottom tray of a transportation box, in accordance with one embodiment.

FIGS. 5*a* and 5*b* illustrate a transportation box 60 for storing the cleaning device system and, optionally, accessories. More specifically, the transportation box may be used to house the device (including shaft and tube set), the module/control box, a filling syringe and tube set, and a USB Type A to USB Type Micro B cable (or other charging cable or mechanism). The transportation box 60 may have two layers, the top layer being shown in FIG. 5*a* and the bottom layer being shown in FIG. 5*b*. In one embodiment, the layers are formed by foam trays. The exact configuration is meant for illustrative purposes only and the transportation box may house the cleaning device system in an alternative configuration.

In the embodiment of FIG. 5*a*, the top tray 62 of the transportation box 60 holds the module or control box 18, a filling syringe and tube set 64, and a microfiber towel and gear ties 66. Storage locations 68 are provided for a plurality of $CO_2$ canisters, the canisters being placed on the lower tray.

In the embodiment of FIG. 5*b*, the bottom tray 70 stores the cleaning device 12, a plurality of $CO_2$ canisters 72, a power supply and power cord 74, and a USB Type A to USB Type Micro B Cable 76. The plurality of $CO_2$ canisters may be, for example, four 16 g $CO_2$ canisters.

Figure 6A:
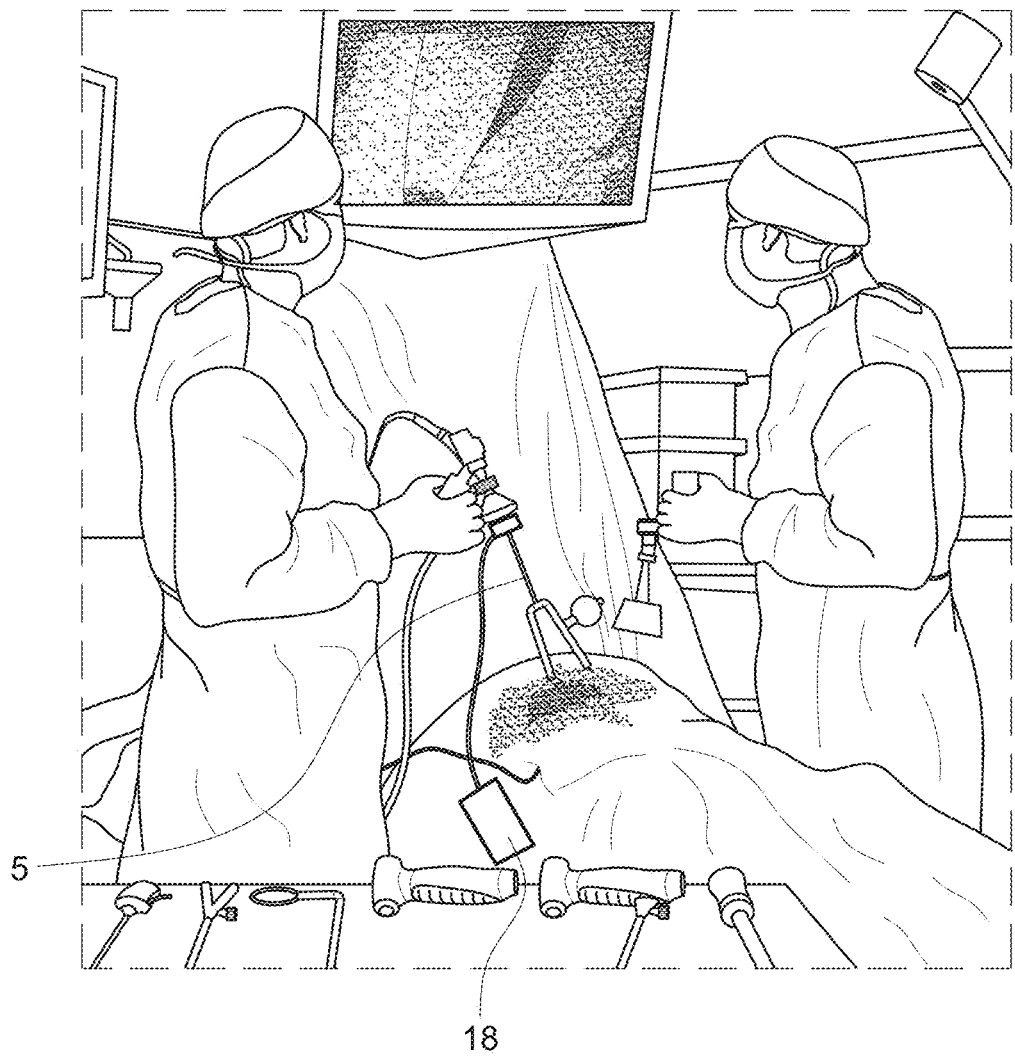
FIG. 6a illustrates the module provided separate from the sheath and control pad such that it may be positioned on an operating room table, in accordance with one embodiment.
Figure 6B:
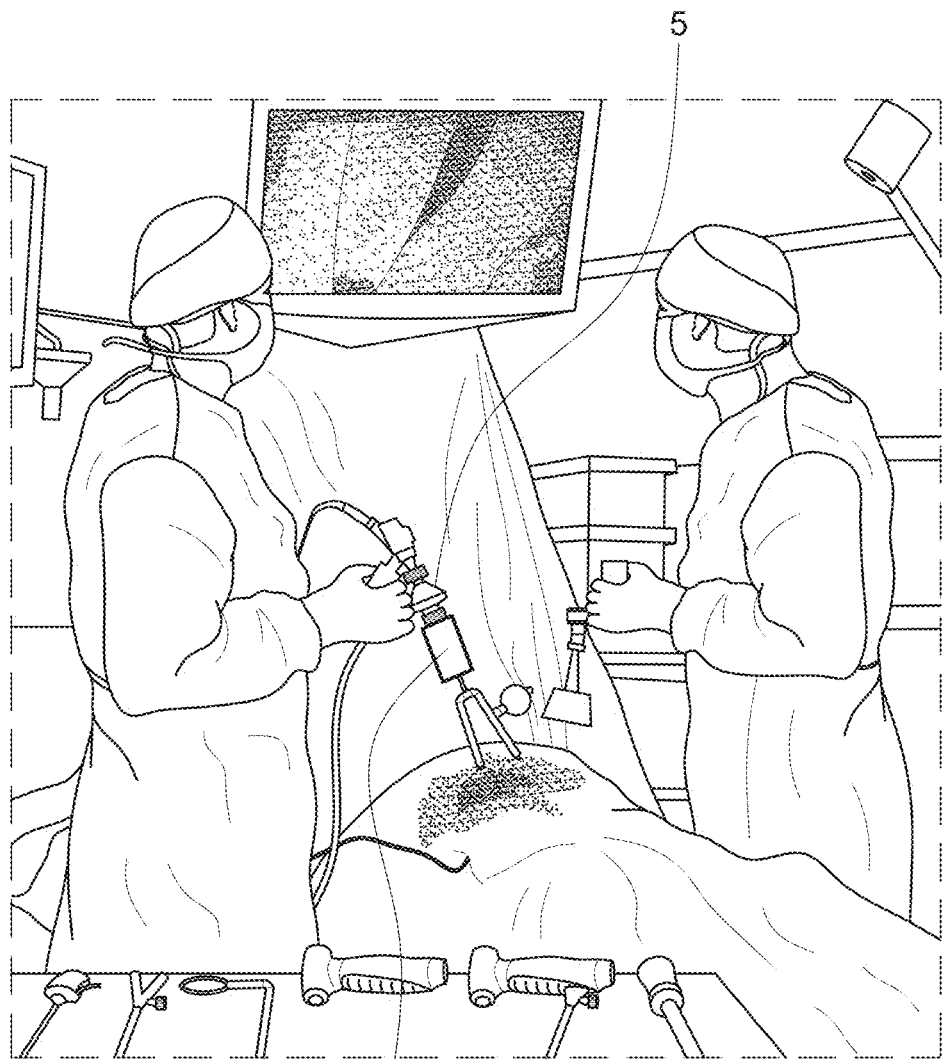
FIG. 6b illustrates the module provided on the shaft of a laparoscope, in accordance with one embodiment.
Figure 6C:
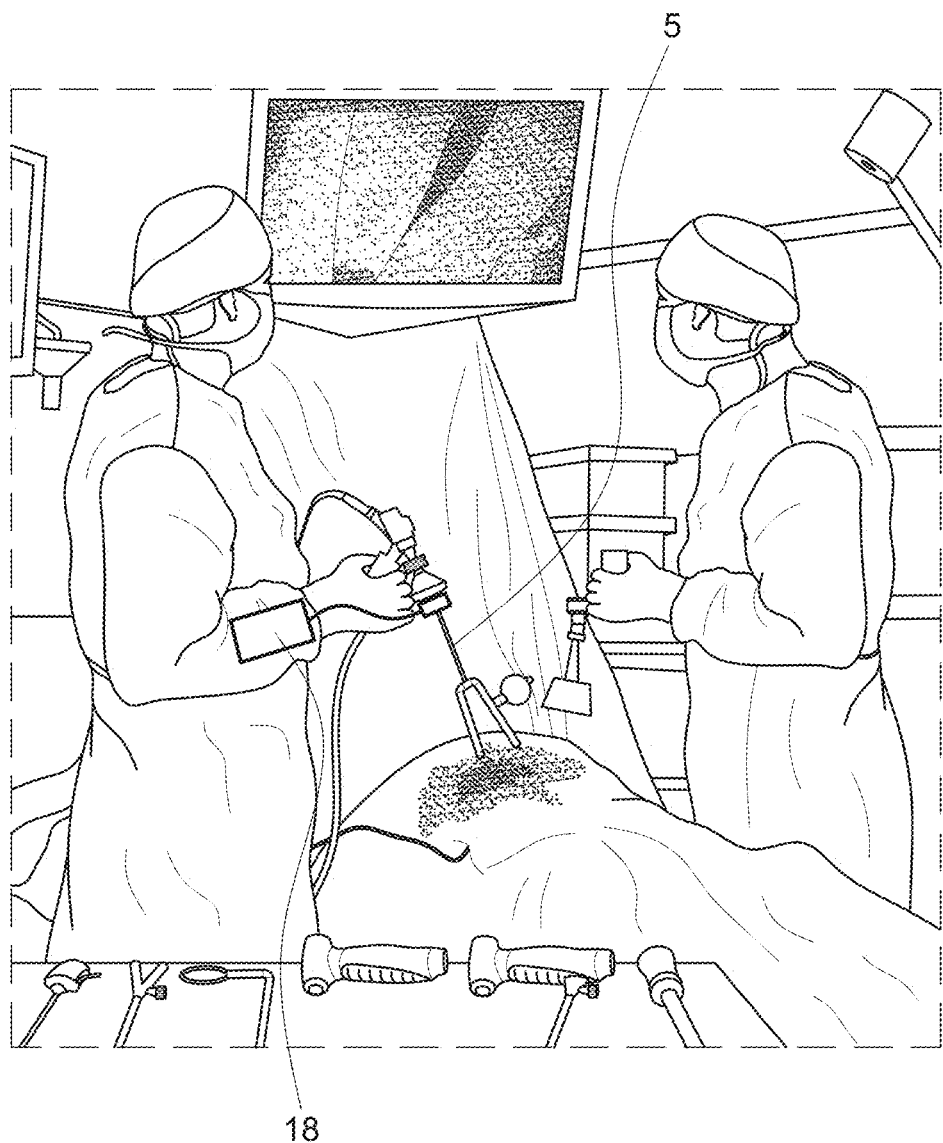
FIG. 6c illustrates the module provided separate from the sheath and control pad and configured to be wearable on the wrist of a user, in accordance with one embodiment.

In various embodiments, during surgery, the module may be provided on the surgical tool shaft, on the cleaning device control pad, or separate from the cleaning device. FIGS. 6a-6c illustrate the module 18 in different positions.

FIG. 6a illustrates the module 18 provided separate from the surgical tool 5 and cleaning device 12 such that it may be positioned on an operating room table.

FIG. 6b illustrates the module 18 provided on the shaft of a surgical tool 5. This embodiment may be useful with, for example, a bariatric laparoscope or other surgical device having a relatively longer shaft length.

FIG. 6c illustrates the module 18 provided separate from the surgical tool 5 and cleaning device 12 and configured to be wearable on the wrist of a user.

Returning to FIG. 1a, the cleaning device system is shown with a laparoscope. The cleaning device 12 is attached to the laparoscope and includes a sheath 14, a nozzle 15, and a control pad 16. In some embodiments, the shaft comprises a hollow tube structure having two channels or lumens, one for a first fluid, such as saline, and one for a second fluid, such as compressed $CO_2$. These channels may be referred to as an irrigation channel and a drying channel. The shaft structure may be sized to the dimension of the scope or other surgical tool. It is to be appreciated that this sizing will vary depending on the surgical device with which the cleaning device is being used. In one embodiment, the shaft may have a tube structure that fits over a Karl Storz scope, P/N 26003 BA (Ø10 mm, 30° tip, 31 mm length) and may be capable of traversing the ID of an Ethicon XCEL Bladeless Trocar with Stability Sleeve 12 mm-100 mm, P/N B12LT.

The shaft of the cleaning device may be formed of any suitable material. For example, the shaft may be formed of extruded plastic or of welded stainless steel. The sheath 14 includes a proximal end interfacing with the control pad 16 and a distal end interfacing with the nozzle 15. The sheath 14 may have a retaining feature 20 for restraining the shaft of the sheath on the surgical device. The sheath may include an irrigation channel and a drying channel. The sheath may further include a heating element channel. In some embodiments more than one irrigation channel, drying channel, or heating element channel may be provided. The sheath 14 may be sized to accommodate a laparoscope shaft or shaft of other surgical device. Thus, for example, if the cleaning device is to be used with a 10 mm laparoscope shaft, the sheath may have an inner diameter of about 10 mm and an outer diameter of about 12 mm. If the cleaning device is to be used with a 5 mm laparoscope sheath, the sheath may have an inner diameter of about 5 mm and an outer diameter of about 7 mm. Accordingly, the thickness of the shaft may be about 2 mm. In alternative embodiments, different inner and outer diameters and different thicknesses may be used. The shaft may have a lubricious interior, whether by manufacture of a lubricious material or by addition of a lubricious coating, to facilitate sliding of the sheath 14 onto a shaft of a surgical tool such as a laparoscope.

In some instances, it may be desirable to warm the irrigation fluid to facilitate clearing of fatty fluids and fog. For example, it may be desirable to warm the fluid to a temperature of at least about 40° C. (104° F.). A heating element thus may be provided to heat the fluid to approximately 40° C. (104° F.). This may be done by heating the fluid in the shaft or at the reservoir. The heating element may be chosen such that it is able to heat the fluid to the desired temperature, for example 40° C., in 10 minutes or less. In various embodiments, the heating element may be a conformal shaft resistive heater. In one embodiment, the heating element comprises a resistive heating wire inserted in a resistive wire lumen. Heating may be achieved in an open- or a closed-loop approach (with or without temperature sensing). The heating element may be provided in a heating element channel of the shaft and powered by the battery in the module. Alternatively, other heating elements or approaches may be used. For example, in another embodiment, the area of the lens, rather than the fluid, may be heated. In such an embodiment, a heated lens may be provided over the laparoscope lens (ITO coating/film).

The sheath and nozzle of the cleaning device are complementary such that channels provided in the sheath engage ports in the nozzle. In one embodiment, the irrigation channel and the drying channel are opposed from one another on opposite sides of the sheath. In another embodiment, the irrigation channel and the drying channel are on the same side of the sheath. In one such embodiment, the irrigation direction is downward and to the right (facing distally) and the jet-dry direction is downward and to the left (facing distally). The cross-sectional area of the irrigation channel and the drying channel may be the same or may be different. In an embodiment using an irrigation channel and a suction channel (as opposed to a drying channel), the irrigation channel may have a larger cross-suction than the vacuum channel to provide for higher velocity.

Figure 7A:
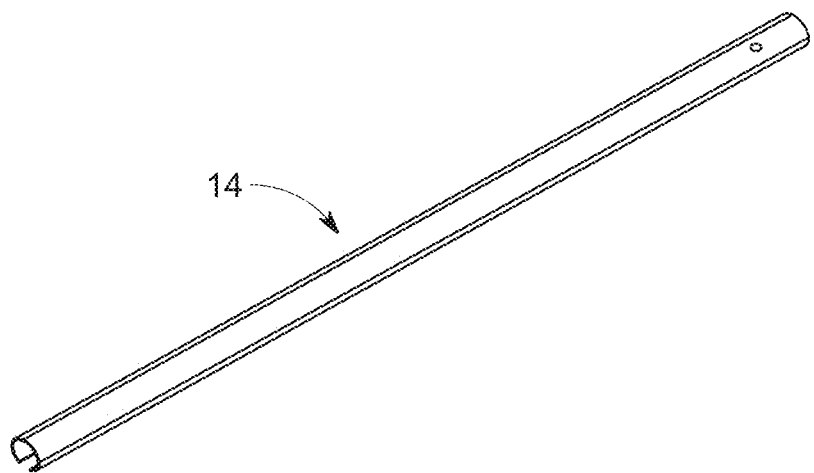
FIG. 7a illustrates a perspective view of a sheath of a cleaning device, in accordance with one embodiment.
Figure 7B:
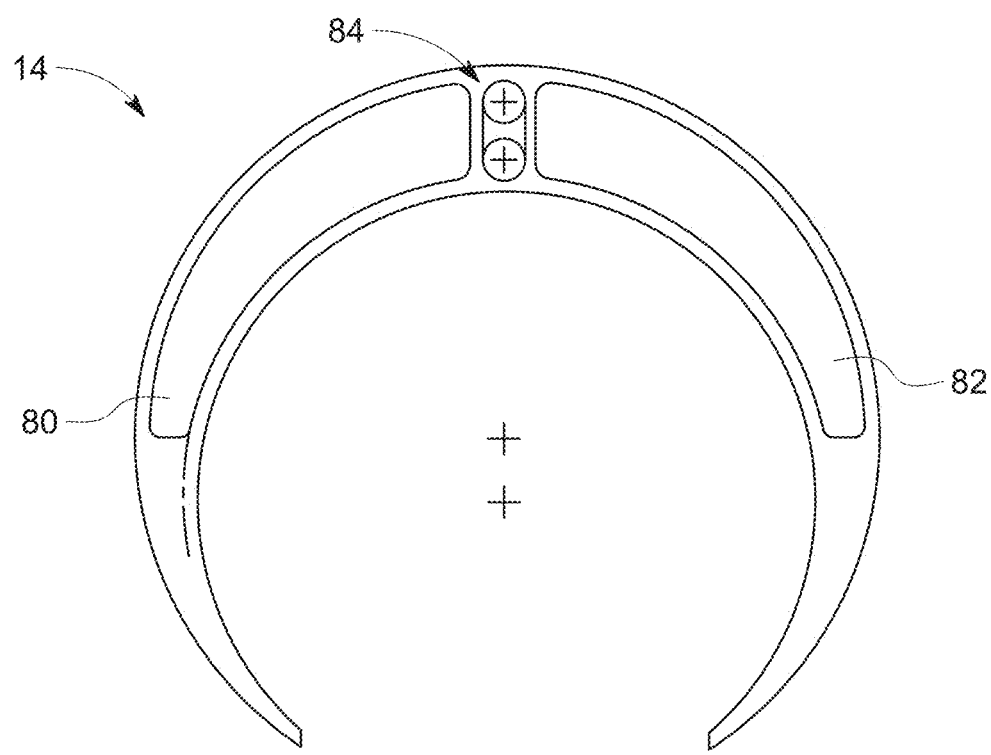
Figure 7C:
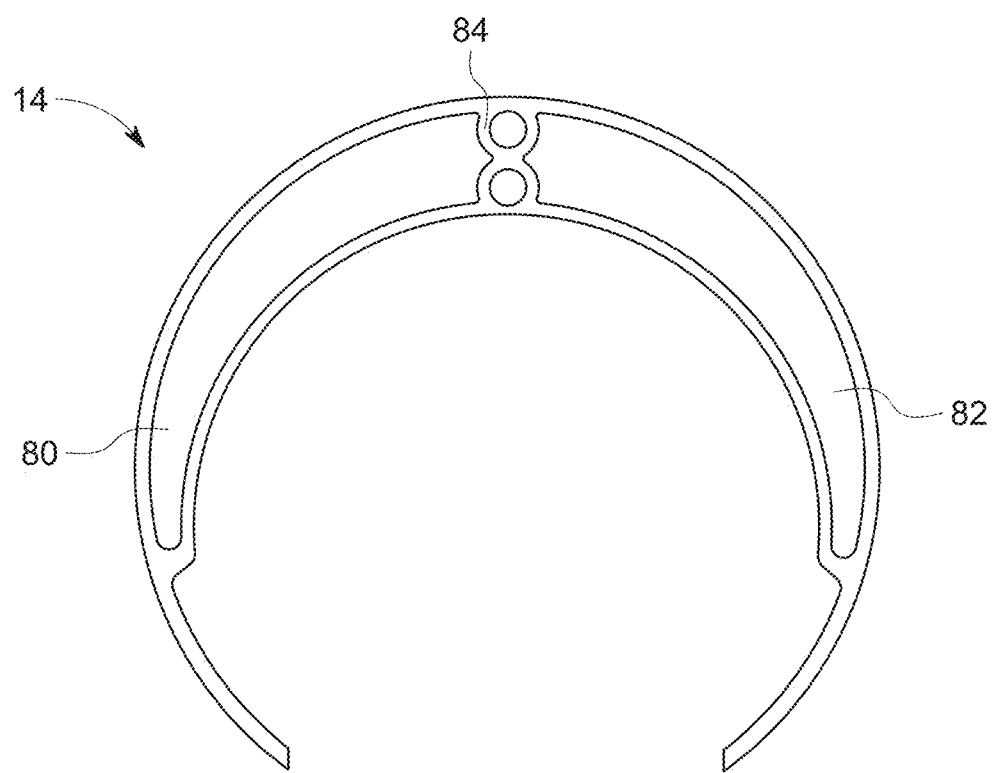

FIGS. 7a, 7b, and 7c illustrate a sheath 14 of a cleaning device wherein the irrigation channel and the drying channel are on the same side of the sheath, in accordance with exemplary embodiments. FIG. 7a illustrates a perspective view of a sheath 14 of a cleaning device, in accordance with one embodiment. As shown, the sheath has a thicker upper wall that tapers alongside walls to an open bottom.

FIGS. 7b and 7c illustrate an end views of a sheath 14 such as shown in FIG. 5a, in accordance with two embodiments. The end view shows an irrigation channel or lumen 80 and a drying channel or lumen 82 in an upper wall of the sheath 14. One or heating channels 84 are provided between the irrigation channel 80 and the drying channel 82. The heating channels 84 may receive resistive wires.

Figure 8A:
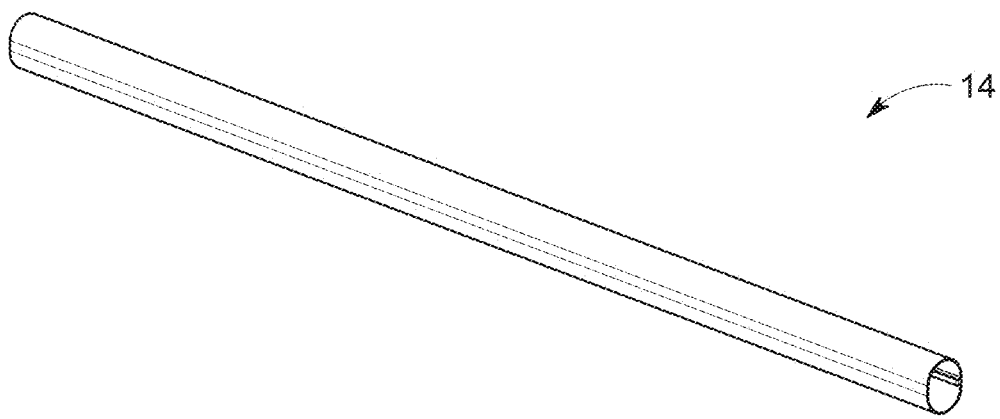
FIG. 8a illustrates a perspective view of a sheath of a cleaning device, in accordance with another embodiment
Figure 8B:
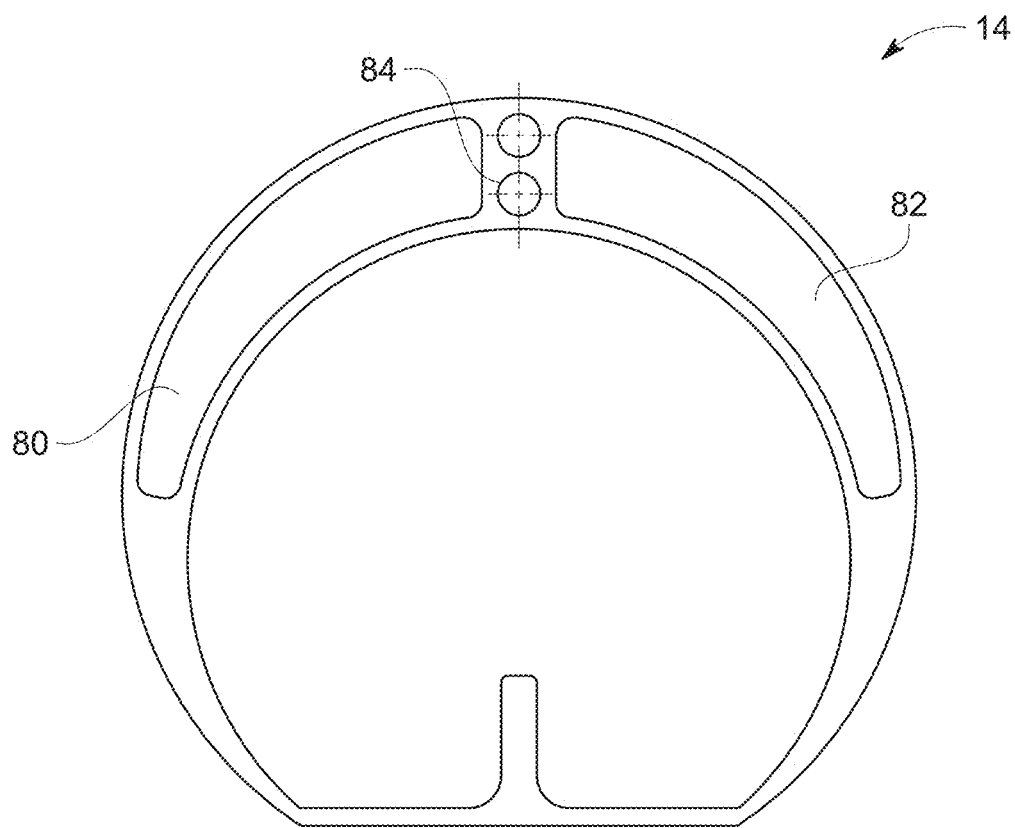

FIGS. 8a and 8b illustrate a variation of the embodiments shown in FIGS. 7a-7c. In the embodiment of FIGS. 8a and 8b, the irrigation channel 80 and drying channel 82 are on the same side of the sheath 14. The sheath 14 has a thicker upper wall that tapers alongside walls to a thin bottom wall.

The nozzle of the cleaning device may have any suitable configuration for generally directing irrigation fluid, and optionally drying fluid, such as $CO_2$, towards the lens. In some embodiments, the irrigation fluid and the drying fluid may be directed towards the lens in the same manner. In other embodiments, the irrigation fluid and the drying fluid may be directed differently, for example with the irrigation fluid being directed at the lens and the drying fluid being directed across the lens.

Figure 9A:
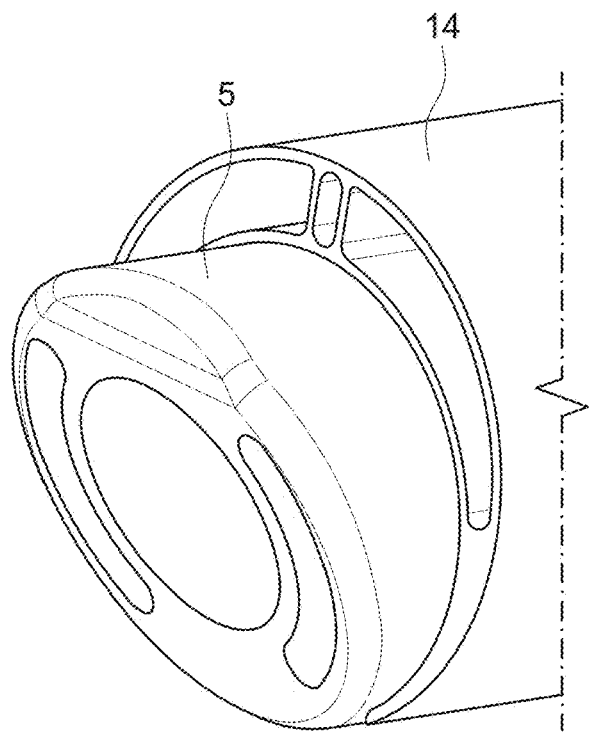
FIG. 9a illustrates an end of a sheath of a cleaning device as positioned on a laparoscope sheath, in accordance with one embodiment.

FIGS. 9a-9d illustrate a nozzle of a cleaning device in accordance with one embodiment. FIG. 9a illustrates an end of a laproscope with a sheath 14 of a cleaning device provided around the shaft of the laparoscope 5 but without a nozzle attached to the sheath 14 of the cleaning device. FIG. 9a illustrates a 30 degree laparoscope 5. As shown, the sheath 14 of the cleaning device may terminate prior to the end of the laparoscope. In alternative embodiments, the sheath 14 of the cleaning device may extend to or past the end of the laparoscope.

Figure 9B:
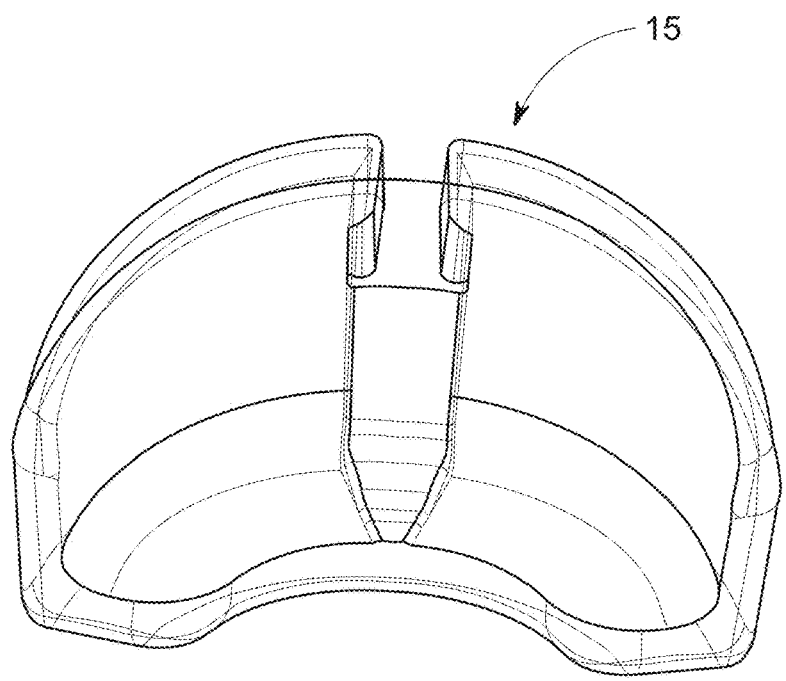
FIG. 9b illustrates a nozzle face for attachment to the sheath of a cleaning device, in accordance with one embodiment.
Figure 9C:
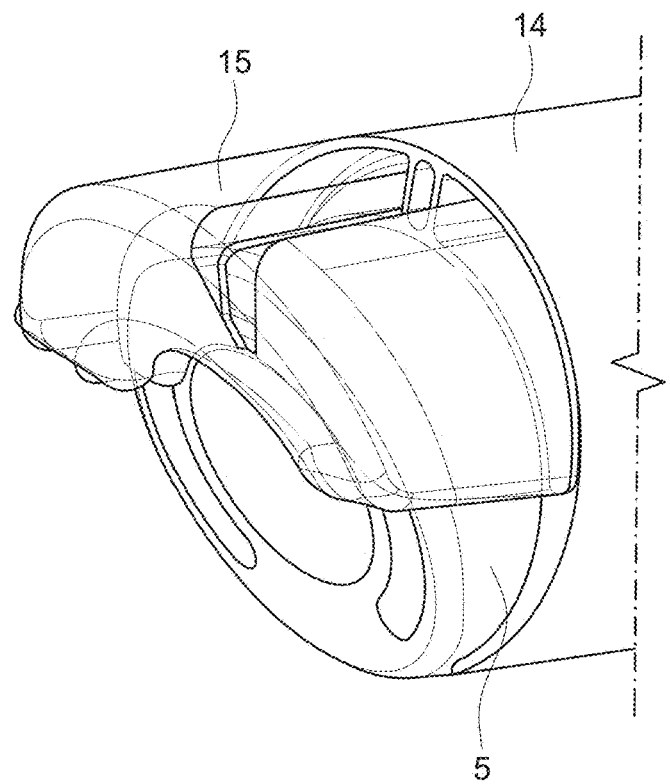
FIG. 9c illustrates the nozzle of FIG. 9b as attached to the sheath of a cleaning device positioned on a laparoscope sheath, in accordance with one embodiment.
Figure 9D:
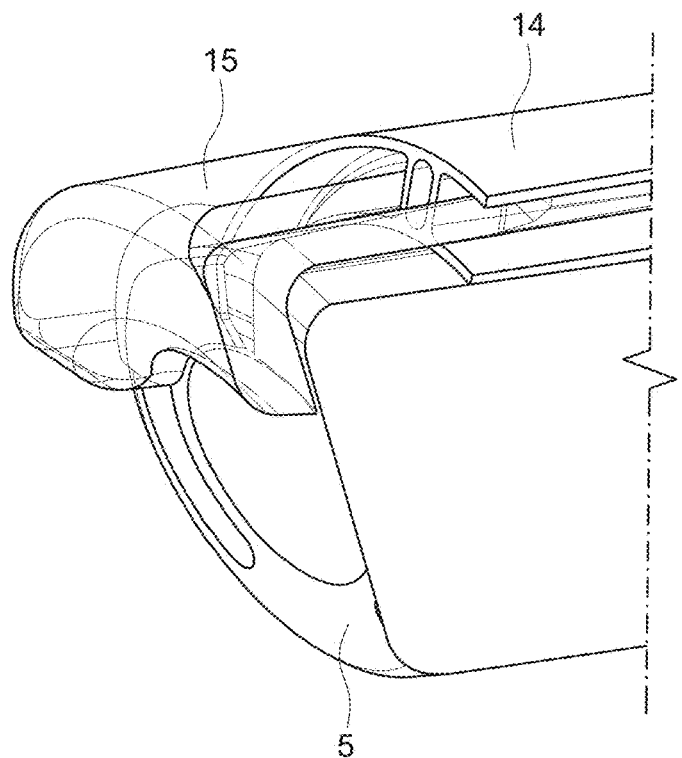
FIG. 9d illustrates the nozzle of FIG. 9b as attached to the sheath of a cleaning device positioned on a laparoscope sheath, in accordance with one embodiment.

FIG. 9b illustrates a nozzle 15 for attachment to the shaft of a cleaning device, in accordance with one embodiment. FIGS. 9c and 9d illustrate the nozzle of FIG. 9b as attached to the sheath 14 of a cleaning device positioned on a laparoscope 5 shaft, in accordance with one embodiment. In the embodiment shown, the nozzle 14 folds over an upper wall of the laparoscope sheath to direct irrigation fluid and air or $CO_2$ for jet drying towards the lens of the laparoscope.

Detail will now be given to set up of the cleaning device system, in accordance with one embodiment.

Figure 10A:
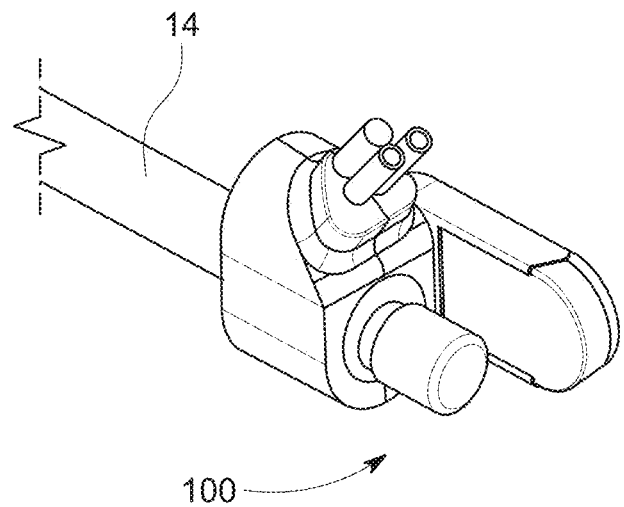
FIG. 10a illustrates an initial optional step in setting up the cleaning device system, in accordance with one embodiment.
Figure 10B:
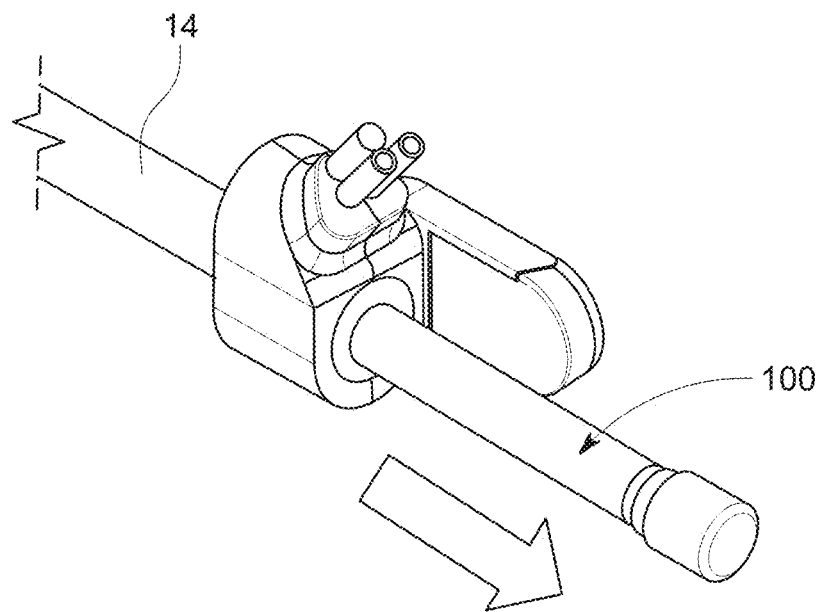
FIG. 10b illustrates an initial optional step in setting up the cleaning device system, in accordance with one embodiment.

FIGS. 10a and 10b illustrate an initial optional step after removing the system from the transportation box. In some embodiments, a shaft support element 100 may be provided in the sheath 14 during storage. An initial step thus is to remove such shaft support element 100 if provided.

Figure 11A:
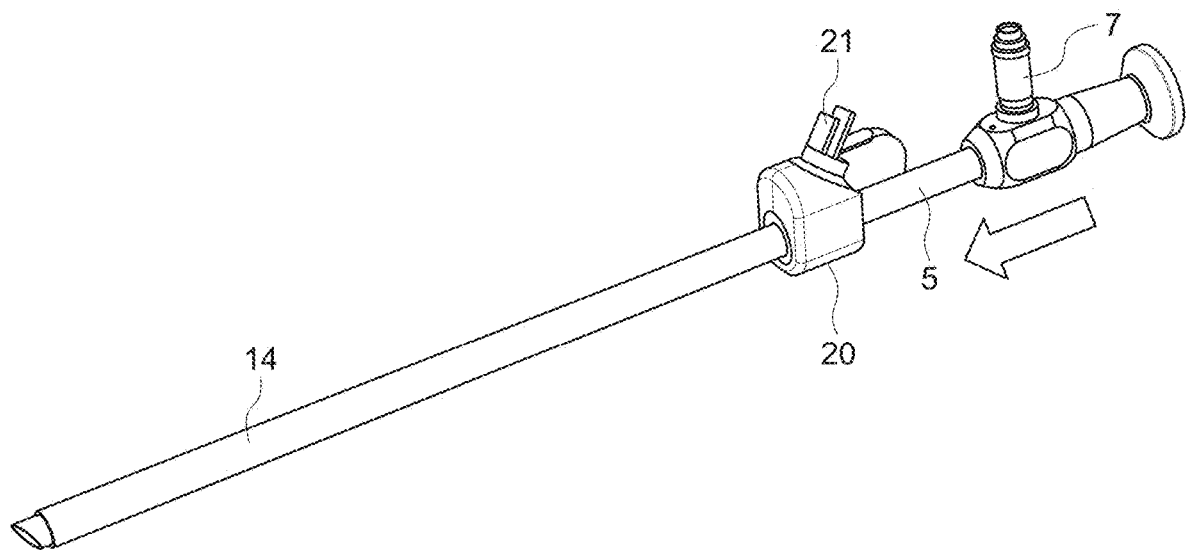
FIG. 11 a illustrates insertion of a laparoscope shaft into the sheath of a cleaning device, in accordance with one embodiment.
FIG. 11b illustrates insertion of a laparoscope shaft into the sheath of a cleaning device, in accordance with one embodiment.
FIG. 11c illustrates a sheath attached to a retaining feature and the retaining feature attached to a laparoscope at the light post of the laparoscope, in accordance with one embodiment.
Figure 11B:
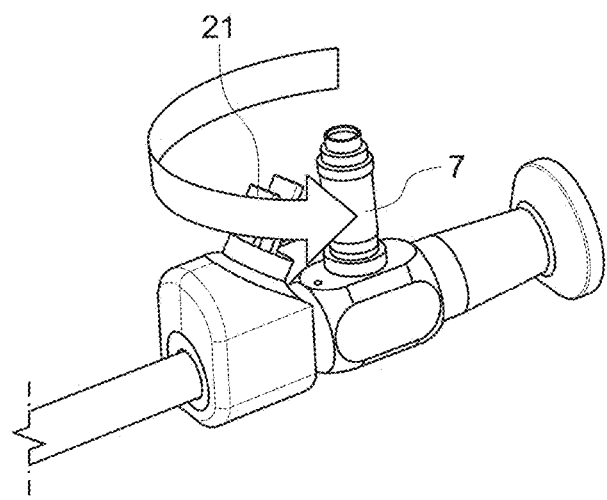

FIGS. 11a and 11b illustrate insertion of a laparoscope shaft into the sheath 14 of the cleaning device and securement of the laparoscope shaft in the sheath 14. FIGS. Ba and Bb illustrate the cleaning device with a Karl Storz scope, P/N 26003 BA (Ø10 mm, 30° tip, 31 mm length). However, the cleaning device may be used with any suitable surgical device or robot and the scope is show for illustrative purposes only.

FIG. 11a illustrates insertion of the scope into the sheath 14. Insertion is through the retaining feature 20. The scope is inserted such that the light post 7 on the laparoscope abuts or nearly abuts the retaining feature 20. The shaft tube set receptors 21 may be coupled to the light post 7 using any suitable mechanism. For example, the shaft tube set receptors 21 may be coupled to the light post 7 using gear ties, as shown in FIG. 11b.

Figure 11C:
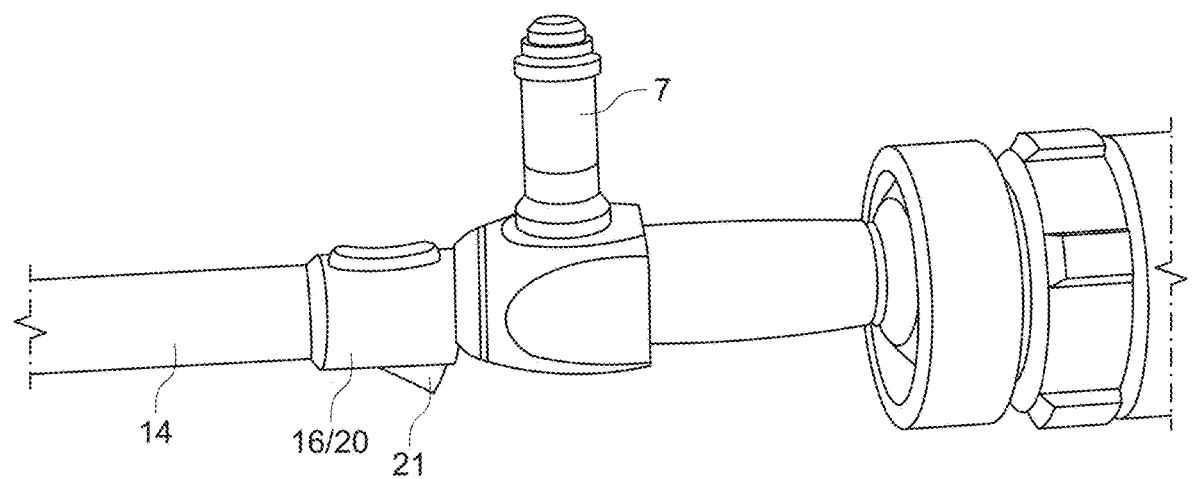

Accordingly, in order to use the cleaning device, the sheath 14 is attached to the retaining feature 20 (optionally holding the control pad 16) and the retaining feature is attached to the laparoscope at the light post 7 of the laparoscope. FIG. 11c illustrates such connection.

The cleaning device may include a tube set and control cable. In one embodiment, the tube set and cable are permanently affixed to the shaft and detachable coupled to the module/control box. In alternative embodiments, either or both of these may be removably coupled to the shaft or permanently affixed to the module/control box. In one embodiment, the tube set and cable are approximately 1000 mm−0/+50 mm in length.

Figure 12A:
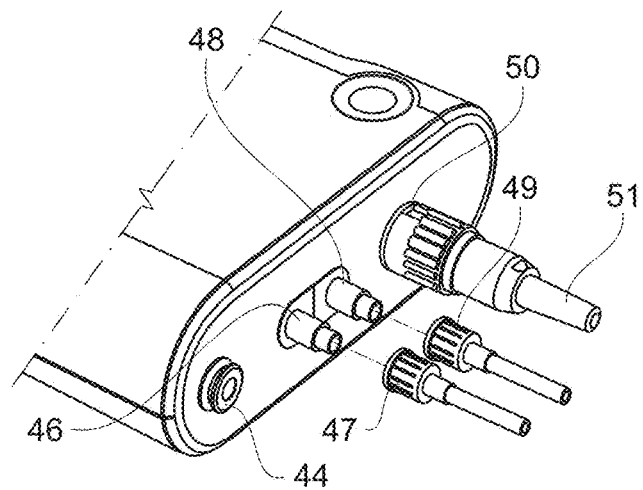
FIG. 12a illustrates connection of tube connectors to ports and an electrical cable to an electrical port, in accordance with one embodiment.
Figure 12B:
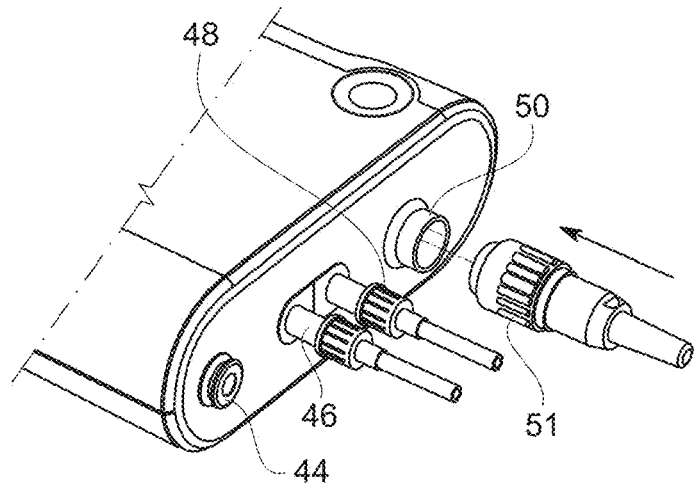
FIG. 12b illustrates connection of tube connectors to ports and an electrical cable to an electrical port, in accordance with one embodiment.
Figure 12C:
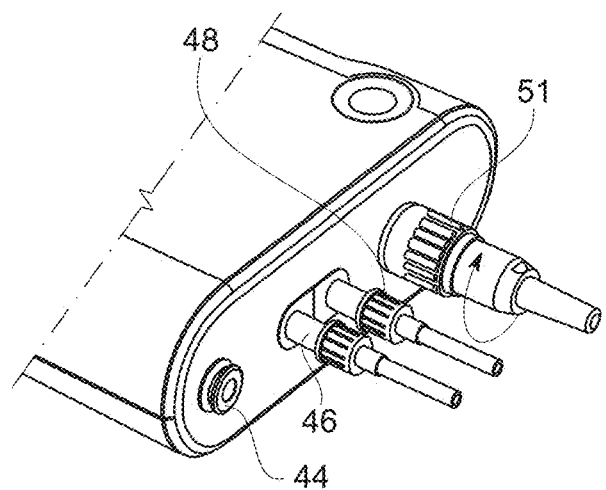
FIG. 12c illustrates connection of tube connectors to ports and an electrical cable to an electrical port, in accordance with one embodiment.

FIGS. 12a-12c illustrate connection of tube connectors 47, 49 to ports 46 and 48 and an electrical cable 51 to the electrical port 50 for an embodiment wherein the tube set is detachably coupled to the module. The tube connectors 47, 49 and ports 46, 48 may be color coded to ensure the correct tube connector 47, 49 is connected to the correct port 46, 48. More specifically, the tube connectors 47, 49 and ports 46, 48 may be color coded to ensure that the saline 47 connector is connected to the saline port 46 and the $CO_2$ (or other fluid) connector 49 is connected to the $CO_2$ (or other fluid) port 48.

FIG. 12a illustrates the module 18 prior to connection of the tube connectors 47, 49 to the ports 46, 48 but after connection of the electrical cable 51 to the electrical port 50. FIG. 12b shows the opposite order of connection with the tube connectors 47, 49 coupled to ports 46, 48 but before connection of the electrical cable 51 to the electrical port 50. FIG. 12c illustrates the module 18 with the tube connectors 47, 49 coupled to ports 46, 48 and the electrical cable 51 coupled to the electrical port 50. In one embodiment, coupling of the electrical cable comprise aligning a connection piece of the electrical cable 51 with the electrical port 50, pushing the connection piece into the port 50 to make a connection, and turning the connection piece to lock it in place.

Figure 13:
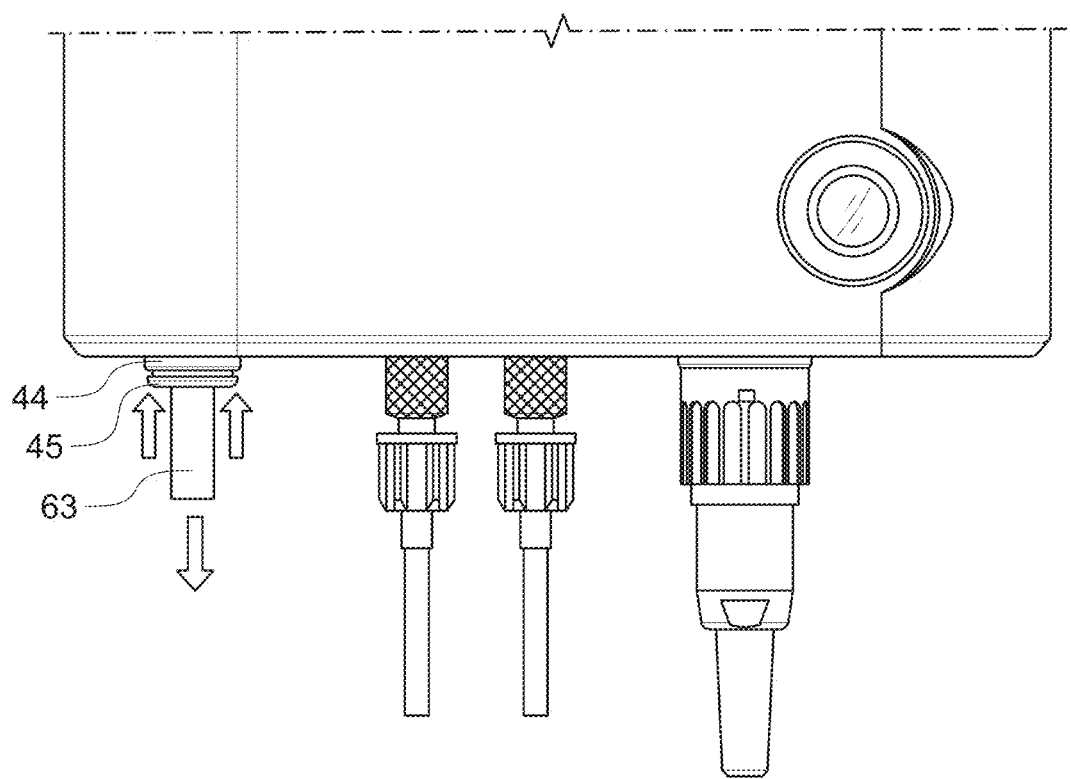
FIG. 13 illustrates removal of a fill syringe tube from a fill port, in accordance with one embodiment.

The internal reservoir of the module is filled using a filling syringe and tube set (62 of FIG. 5a). This may be done, for example, by inserting the tube into the push-to connect fill port 44. In one embodiment, to fill the reservoir, the power switch must be in the off position to allow air behind the piston cylinder to vent during the fill process. FIG. 13 illustrates removal of the fill syringe tube 63 of the filling syringe and tube set 62 from the fill port 44. In one embodiment this may be done by pressing inwardly on a collar 45 surrounding the fill syringe tube and pulling the tube away from the port 44.

Figure 14A:
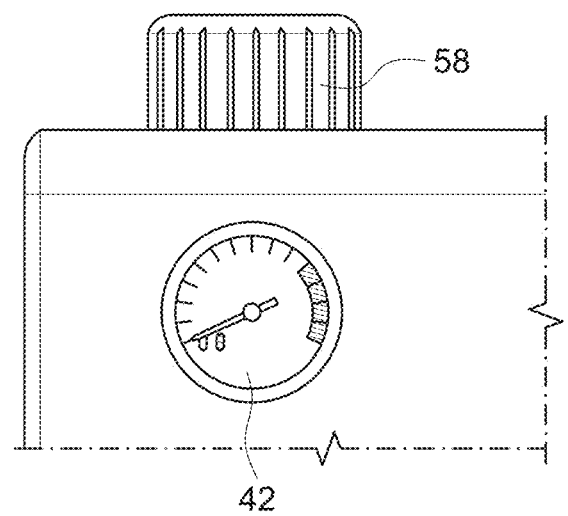
FIG. 14a illustrates review of pressure after filling a reservoir, in accordance with one embodiment.
Figure 14B:
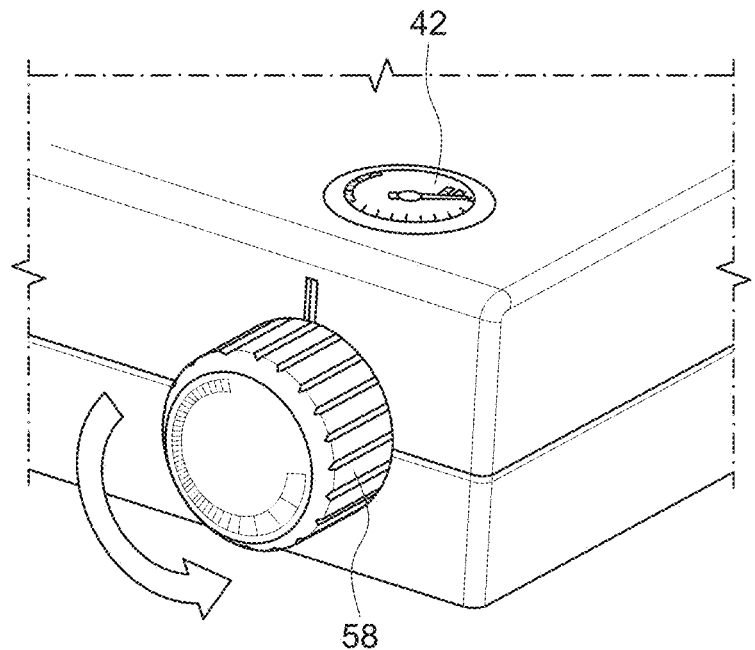
FIG. 14b illustrates review of pressure after filling a reservoir, in accordance with one embodiment.

FIGS. 14a and 14b illustrate review of pressure after filling the reservoir. The pressure gauge or regulator 42 is inspected to ensure that the pressure is set to zero pounds per square inch (psi). The pressure adjustment knob 58 may be used to adjust pressure as necessary.

Figure 15A:
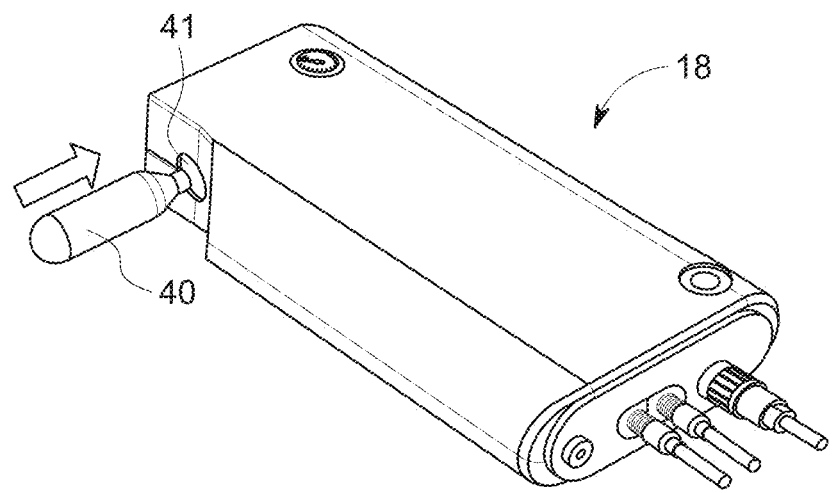
FIG. 15a illustrates installation of a $CO_2$ canister or cartridge, in accordance with one embodiment.
Figure 15B:
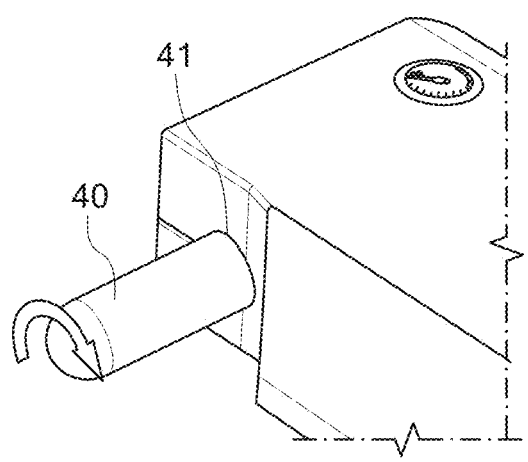
FIG. 15b illustrates installation of a $CO_2$ canister or cartridge, in accordance with one embodiment.

FIGS. 15a and 15b illustrate installation of a $CO_2$ canister or cartridge 40, in accordance with one embodiment. The $CO_2$ cartridge 40 may be, for example, a 16 g $CO_2$ cartridge. The $CO_2$ cartridge 40 is threaded into a $CO_2$ port 41 on the module 18. As the closed end of the $CO_2$ cartridge 40 is pierced, threading force will decrease. Threading should be continued until the connection is hand tight. Alternatively, connection of the $CO_2$ cartridge 40 to the port 41 may not be done by threading and may be done by other suitable mechanism, such as by press fit.

After the $CO_2$ cartridge is installed the pressure may be adjusted to a desired pressure, generally within the range of 0-80 psi, using the pressure adjustment knob 58. For example, the pressure may be adjusted to 40 psi. The power supply may be plugged into the module and connected to power and the power switch may be toggled on. When the power is turned on, a light may be activated to show that power is on. The thermal adjustment knob (54 in FIG. 4b) may be used to adjust power to the heating element as desired. The prime button (53 of FIG. 4b) is pressed until a small amount of saline is dispensed from the nozzle. At this point, the device is ready for use.

Detail will now be given to use of the cleaning device system, in accordance with one embodiment. In use, the camera, laparoscope, and light source function as normal. Light from the laparoscope continues to function through the clear tip of the shaft. A default mode may be set for pulsed $CO_2$.

The control pad may be used to activate cleaning. The buttons on the control pad control use of the cleaning device. As described with respect to FIG. 3a, these buttons may comprise, for example a cycle button 30, activating both irrigation and drying, and a drying button 32 activating drying only. A single press of the clean cycle button results in a short burst of saline followed by a jet of $CO_2$ at the nozzle. The drying button may be programmed to operate in one of two modes: pulsed and continuous. In pulsed mode, a single press of the $CO_2$ button results in release of $CO_2$ in a programmed number of $CO_2$ bursts. In continuous mode, pressing the $CO_2$ button will directly control the duration of $CO_2$ dispensing. To conserve $CO_2$ and prevent freezing of the $CO_2$ cylinder, the continuous dispense mode may be programmed with a limit on the dispense duration while holding the $CO_2$ button. Following a clean cycle, it may be desirable to leave a short period of time without cleaning for the fluid to re-heat in the shaft. If $CO_2$ runs out during the procedure, the cartridge may be replaced by removing it from its location on the module and replacing it. Similarly, if the reservoir empties during the procedure, the reservoir may be refilled using the fill syringe.

The cleaning device may be programmed to customize the cycle and $CO_2$ parameters. Specifically, variables controlling the clean cycle and the $CO_2$ cycle may be modified to achieve different system function such as shorter burst time, longer lockout delay, etc.

Clean cycle variables may include saline dispense time (e.g., 100 milliseconds), delay between dispensing saline and $CO_2$ variable (e.g., 500 milliseconds), and $CO_2$ dispense time variable (e.g., 800 milliseconds).

$CO_2$ variables may be based on whether the system runs in continuous $CO_2$ mod or pulsed $CO_2$ mode. Variables in continuous $CO_2$ may include $CO_2$ run time variable (e.g., 500 milliseconds) and system recovery time variable (e.g., 2000 milliseconds). Variables for pulsed $CO_2$ may include number of pulses variable (e.g., 8) and pulse duration variable (e.g., 25 milliseconds).

Various exemplary configurations of components of the cleaning device system are shown in FIGS. 16a-20g.

FIGS. 16a-16d illustrate a distal end of an extruded plastic sheath 14 of a cleaning device and a nozzle 15 of a cleaning device, in accordance with one embodiment. In this embodiment, the irrigation channel or lumen 80 and the drying channel or lumen 82 are provided opposite one another. As shown, the irrigation channel 80 may comprise two irrigation channels 80. One or heating channels 84 may be provided proximate the irrigation channel 80. In an embodiment with two irrigation channels 80, the heating channel(s) 84 may be provided between the two irrigation channels 80. The heating channel(s) 84 may receive resistive wire(s).

Figure 16A:
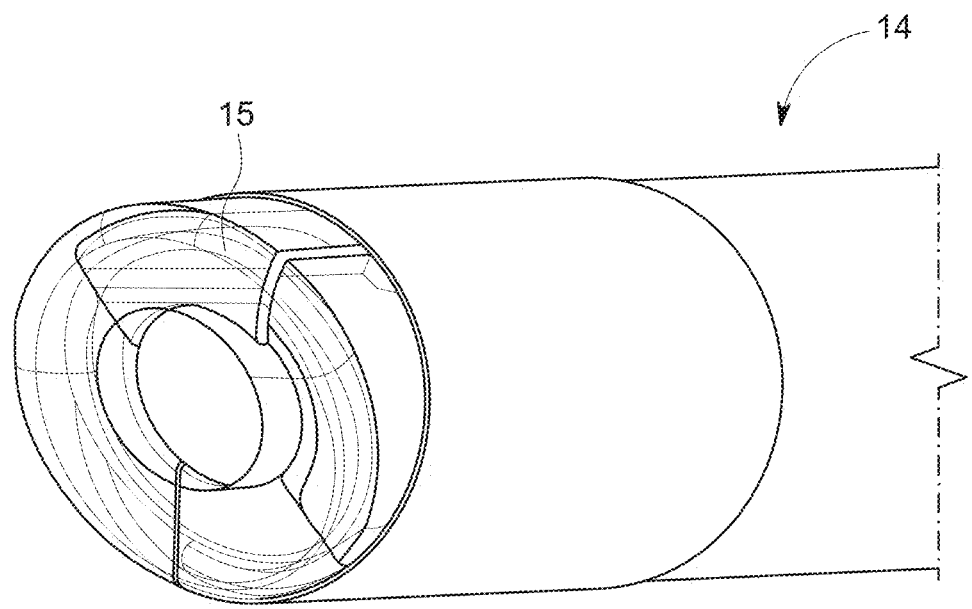
FIG. 16a illustrate an extruded plastic sheath having an injection molded tip with a nozzle attached to the sheath tip, in accordance with one embodiment.
Figure 16B:
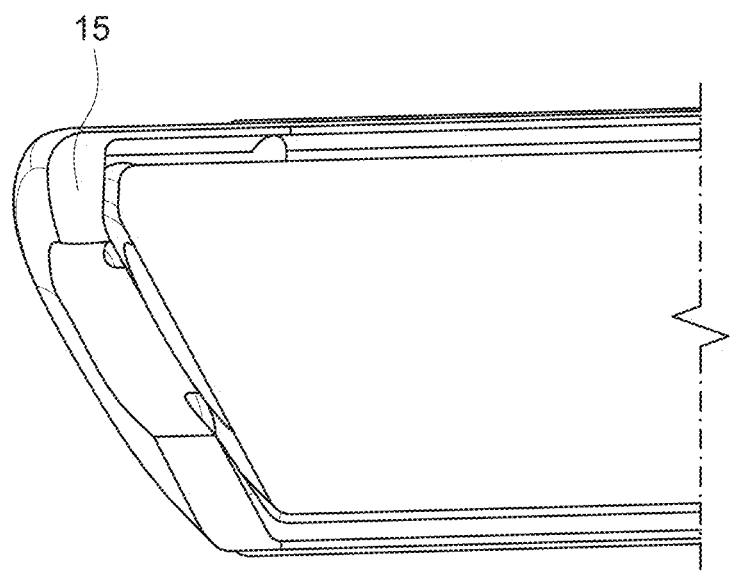
FIG. 16b illustrate an extruded plastic sheath having an injection molded tip with a nozzle attached to the sheath tip, in accordance with one embodiment.
Figure 16C:
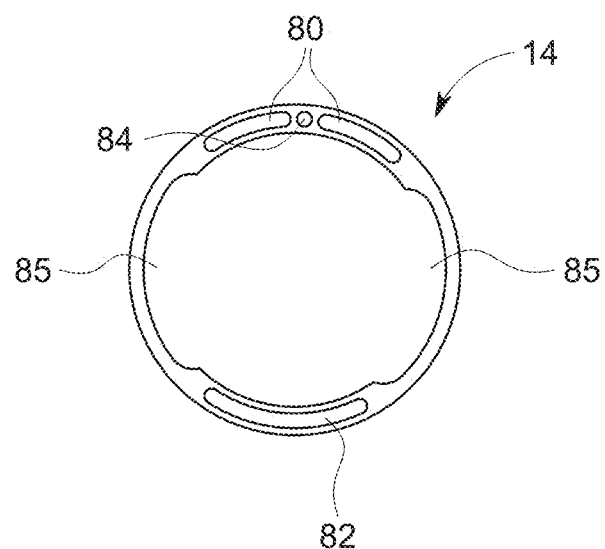
Figure 16D:
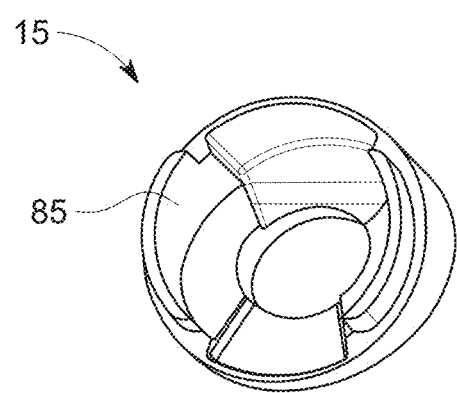
FIG. 16d illustrates a rear view of a nozzle of a cleaning device, in accordance with on embodiment

FIGS. 16a and 16b illustrate an extruded plastic sheath 14 having an injection molded tip with a nozzle 15 attached to the shaft tip. FIG. 16c illustrates an end view of the injection molded tip. In the embodiment shown, two irrigation channels 80 and a heating element channel 84 are provided on a first side of the sheath 14 and a drying channel 82, or $CO_2$ channel, is provided on a second side of the sheath 14 opposite the first side of the sheath 14. Tip keys notches 85 are provided in the sheath 14. FIG. 16d illustrates a rear view of a nozzle 15 of a cleaning device, in accordance with on embodiment. As shown, the nozzle 15 includes tip keys 85 for engaging the tip key notches of the sheath 14. While tip keys and tip key notches are one manner of coupling the nozzle 15 to the sheath 14, it is to be appreciated that any suitable mechanism for coupling the nozzle 15 to the sheath 14 may be used. For example, the nozzle 15 may be press fit or threaded to the sheath 14.

Figure 17A:
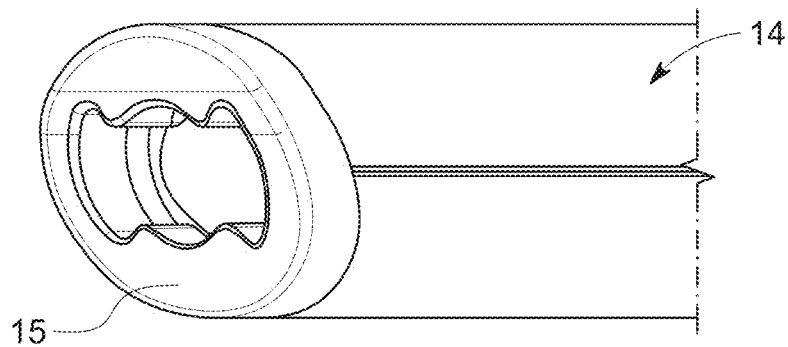
FIG. 17a illustrates a distal end of a welded stainless steel sheath of a cleaning device and a nozzle of a cleaning device, in accordance with one embodiment.
Figure 17B:
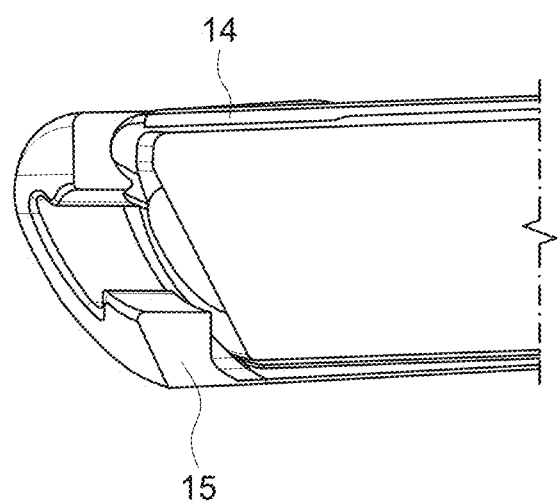
FIG. 17b illustrates a distal end of a welded stainless steel sheath of a cleaning device and a nozzle of a cleaning device, in accordance with one embodiment.
Figure 17C:
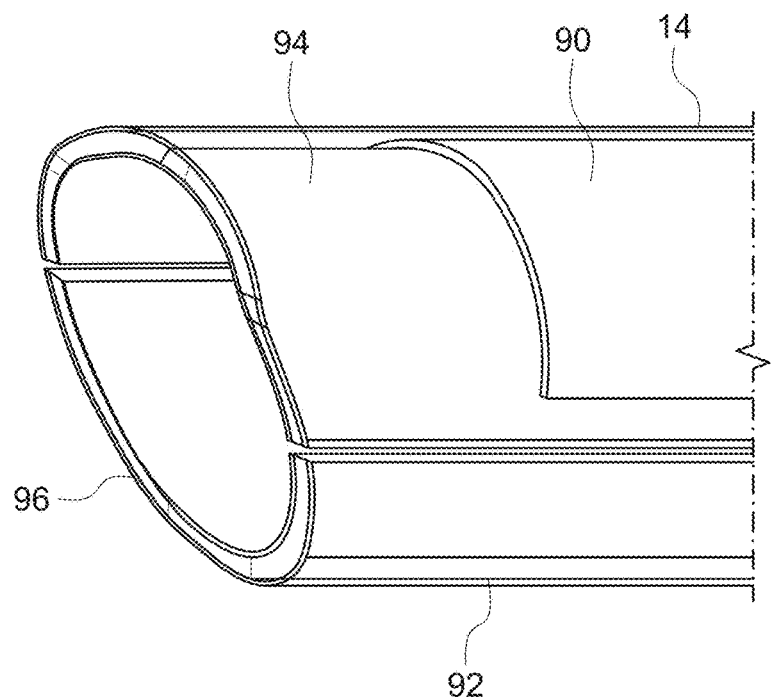
FIG. 17c illustrates a distal end of a welded stainless steel sheath of a cleaning device and a nozzle of a cleaning device, in accordance with one embodiment.
Figure 17D:
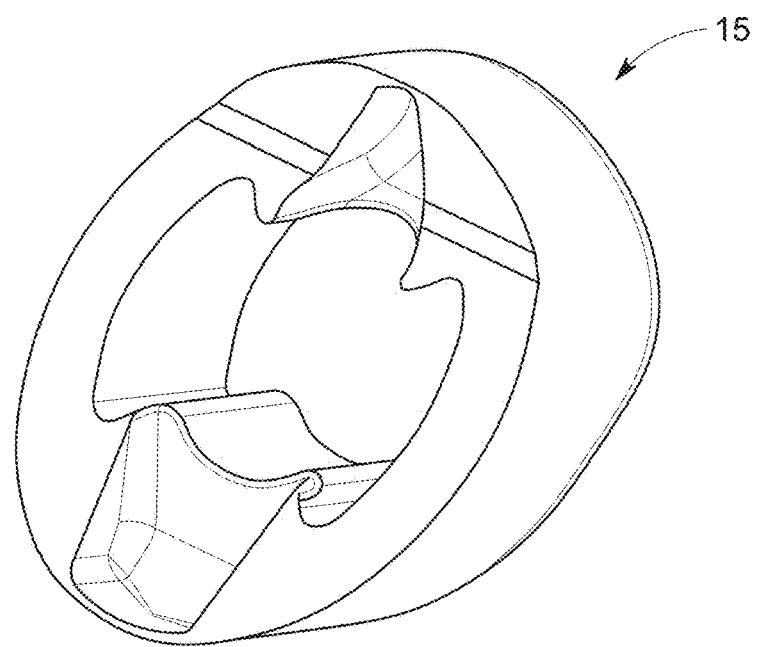
FIG. 17d illustrates a distal end of a welded stainless steel sheath of a cleaning device and a nozzle of a cleaning device, in accordance with one embodiment.
Figure 18A:
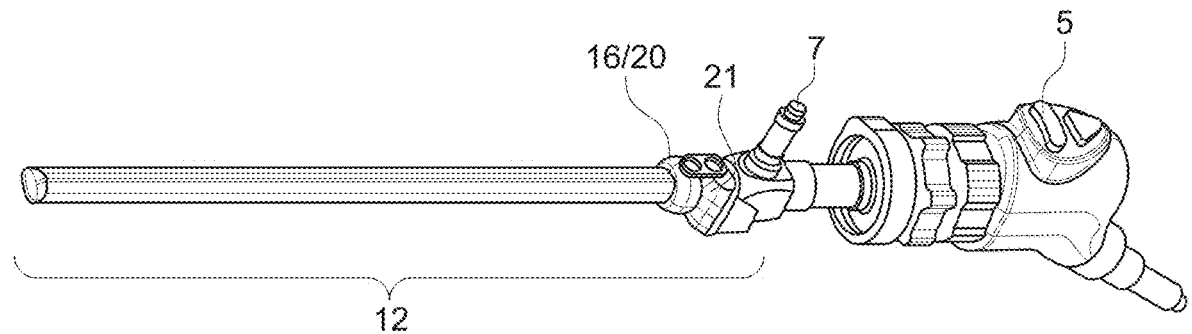
FIG. 18a illustrates various aspects of a cleaning device for use with a laparoscope, in accordance with one embodiment.
Figure 18B:
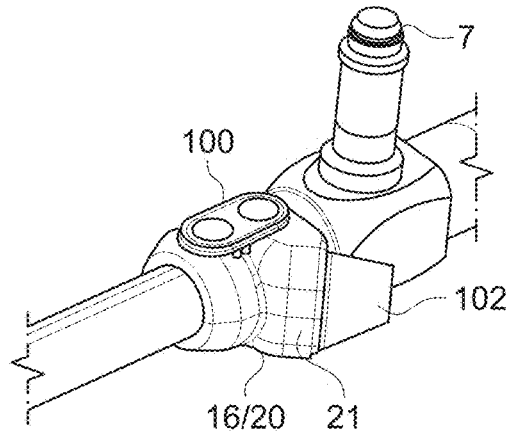
FIG. 18b illustrates various aspects of a cleaning device for use with a laparoscope, in accordance with one embodiment.
Figure 18C:
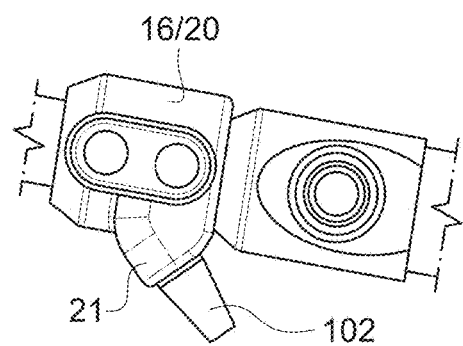
FIG. 18c illustrates various aspects of a cleaning device for use with a laparoscope, in accordance with one embodiment.
Figure 18D:
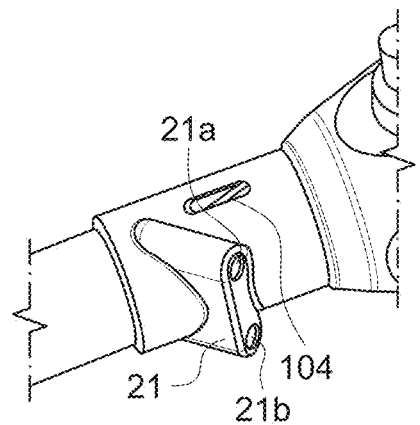
FIG. 18d illustrates various aspects of a cleaning device for use with a laparoscope, in accordance with one embodiment.
Figure 18E:
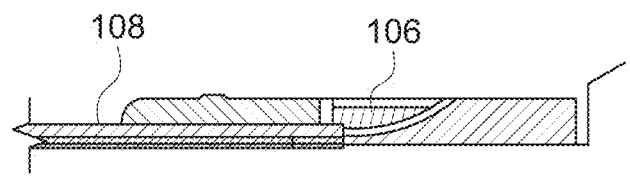
FIG. 18e illustrates various aspects of a cleaning device for use with a laparoscope, in accordance with one embodiment.
Figure 18F:
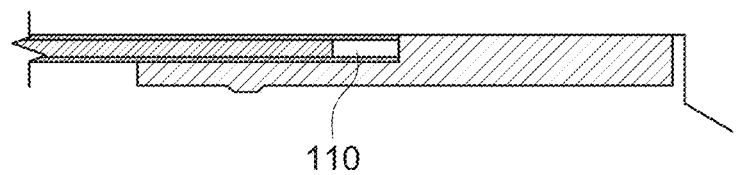
FIG. 18f illustrates various aspects of a cleaning device for use with a laparoscope, in accordance with one embodiment.

FIGS. 17a-17d illustrate a distal end of a welded stainless steel sheath 14 and a nozzle 15 of a cleaning device with a heating element 90 layered into the sheath 14, in accordance with one embodiment. FIG. 17a illustrates a perspective view. FIG. 17b illustrates a cross sectional view. FIG. 17c illustrates a cut away view of the sheath 14 only. FIG. 17d illustrates a perspective view of the nozzle 15 only. The shaft may be formed by laser cut, formed, and/or welded assembly. The tip may be a machined metal tip.

As shown in FIG. 17c, the shaft may have an outer wall 92 and an inner wall 94, with a heating element 90 provided between the outer wall 92 and the inner wall 94 on one side of the sheath 14. The outer wall 92 and inner wall 94 may be welded together at a weld point such as shown at 96.

FIGS. 18a-18f illustrate various aspects of a cleaning device 12 for use with a laparoscope 5, in accordance with one embodiment. In the embodiment shown in FIGS. 18a-18f, the retaining feature 20 is integrated with the control pad 16. Shaft tube receptors 21 are shown and may include an irrigation tube receptor 21a and a jet dry tube receptor 21b, for example. A strain relief element 102 may be provided at the cable/tubing exit. A membrane switch 100 may be provided on the control pad retaining feature 16/20.

A heating element port 104 and heating element channel 106 may be provided for receiving a heating element.

Attachment may done using connection of injection molded control pad retaining feature 16/20 to an extruded sheath 14 via a lapped joint or extrusion 108. An open end of extrusion may closed with an adhesive plug 110. The plug 110 provides strain relief on the heating element, for example on heating element wires. In this embodiment, a two-button membrane switch 100 is provided to control irrigation and jet-dry functionality. Single strain relief element 102 combines the irrigation tube, jet-dry tube, and electrical cable (switch and heating element conductors). While this embodiment is specifically discussed with respect to jet-drying, it is to be appreciated that it may also be used with vacuum drying.

Figure 19A:
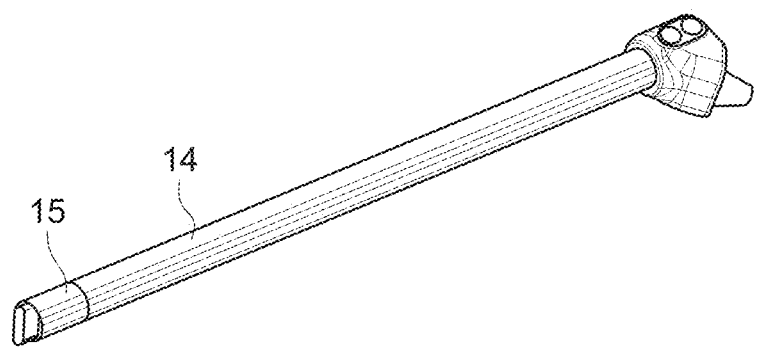
FIG. 19a illustrates a sheath of a cleaning device, in accordance with another embodiment.
Figure 19B:
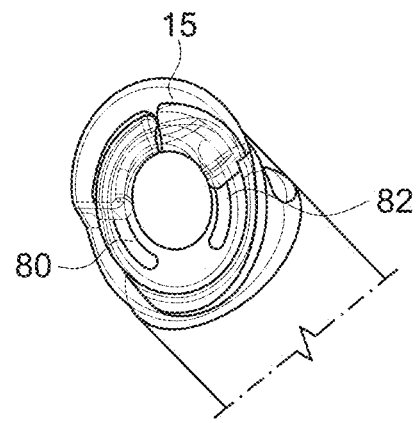
Figure 19C:
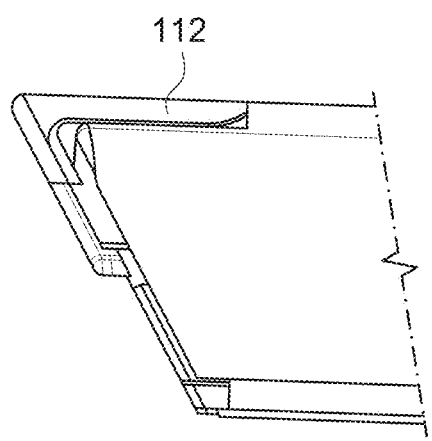
Figure 20A:
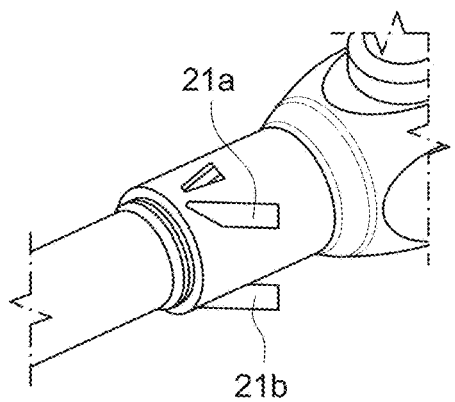
FIG. 20a illustrates attachment of a sheath, in accordance with one embodiment.
Figure 20B:
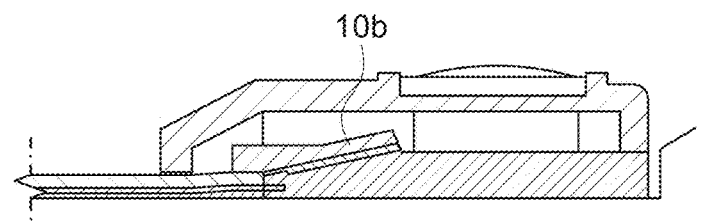
FIG. 20b illustrates attachment of a sheath, in accordance with one embodiment.
Figure 20C:
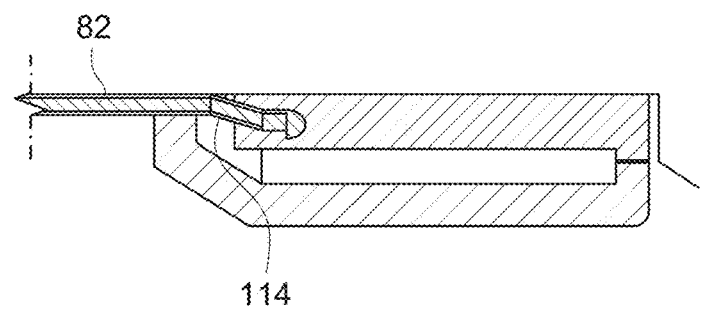
FIG. 20c illustrates attachment of a sheath, in accordance with one embodiment.
Figure 20D:
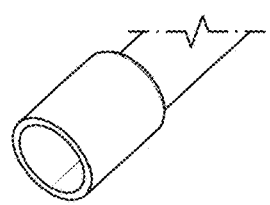
FIG. 20d illustrates attachment of a sheath, in accordance with one embodiment.

FIGS. 19a-19c illustrate a lapped extrusion embodiment similar to that of FIGS. 18a-18f but with the irrigation and drying channels 80, 82 on the same side of the sheath 14, without a lip on the bottom edge of the nozzle, and with a lap joint 112 on connection of the nozzle 15 with the sheath 14.

FIGS. 20a-20d illustrate attachment of the sheath, in accordance with yet another embodiment. In the embodiment shown, attachment is done using connection of by providing injection molded components in the control pad 16 and attaching such components to the shaft using flared extrusion 114. In this embodiment, a two-button membrane switch is provided to control irrigation and jet-dry functionality. Single strain relief combines the irrigation tube, jet-dry tube, and electrical cable (switch and heating element conductors). While this embodiment is specifically discussed with respect to jet-drying, it is to be appreciated that it may also be used with vacuum drying.

Various exemplary schematics and layouts of embodiments of the cleaning device system are shown in FIGS. 21a-27b.

Figure 21A:
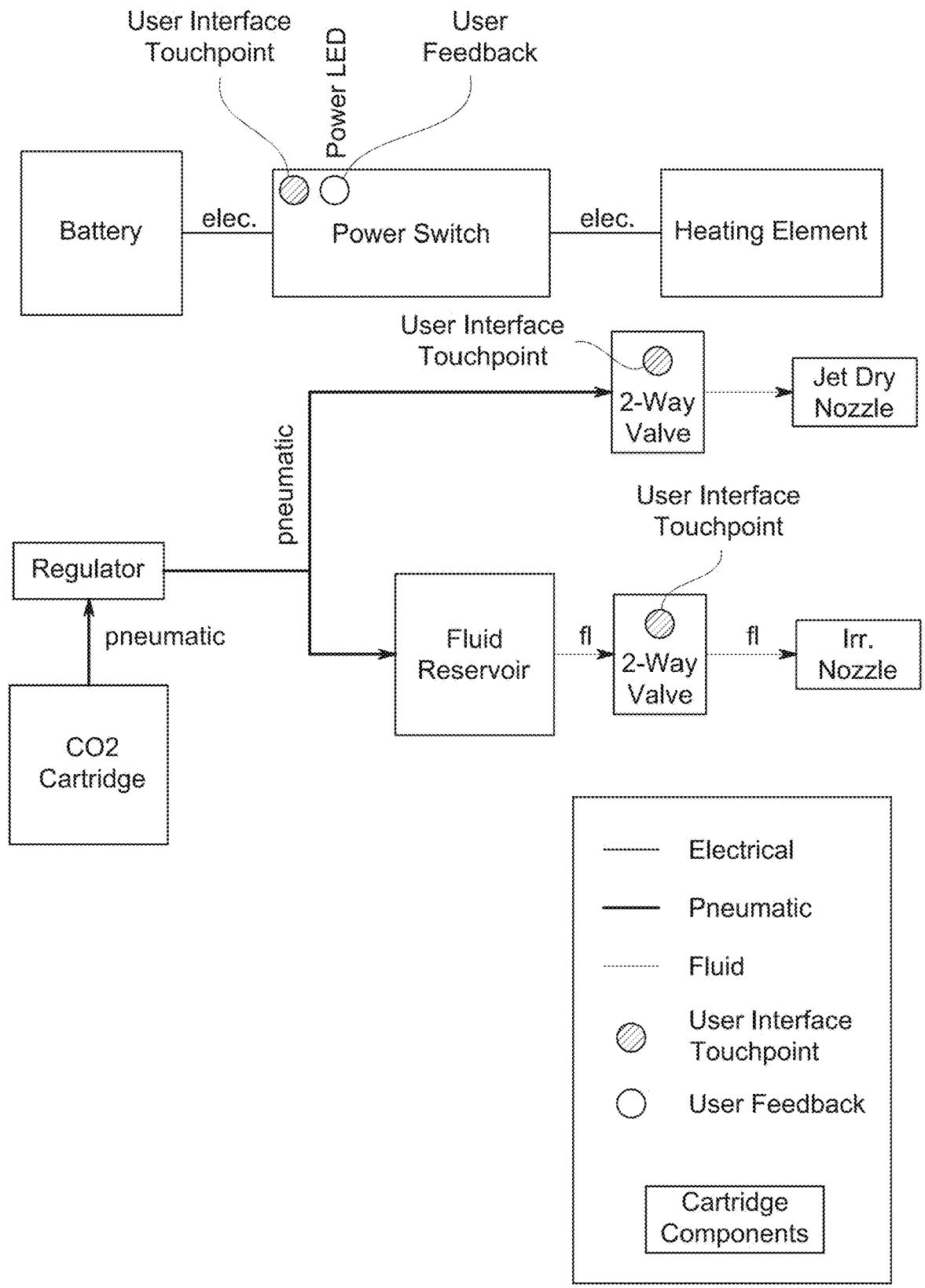
FIG. 21a illustrates a schematic for an embodiment of a cleaning device using jet drying.
Figure 21B:
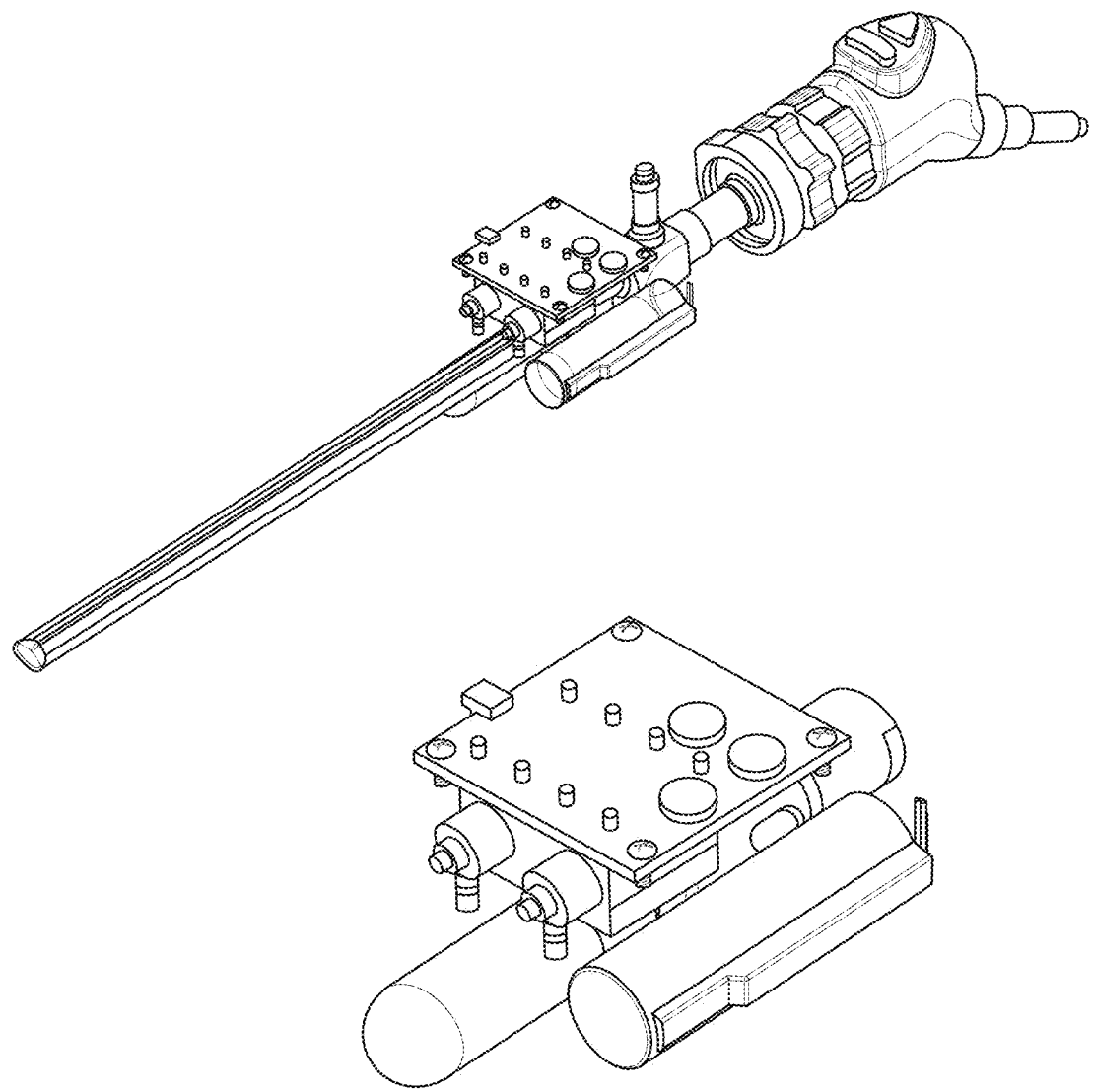
FIG. 21b illustrates a layout for an embodiment of a cleaning device using jet drying.

FIGS. 21a and 21b illustrate a schematic and layout for an embodiment of a cleaning device using jet drying. As shown, the cleaning device includes a battery, $CO_2$ cartridge, and fluid reservoir. These may be provided in a module as described above. A power switch is provided for a user to actuate to turn on the battery and thus heat the heating element. The heating element may be, for example, a conformal resistive shaft heater. The heater may be a heated coil tubing that combines tubing, heating element, and temperature sensing into one unit.

Two two-way valves are provided, actuated by button on the control pad. The two-way valves may be mechanical valves or solenoid valves. The first button turns on the jet dry nozzle, the second button turns on the irrigation nozzle. Each of the irrigation and the jet dry are powered by the $CO_2$ cartridge. The irrigation nozzle is fed fluid from the fluid reservoir.

Figure 22A:
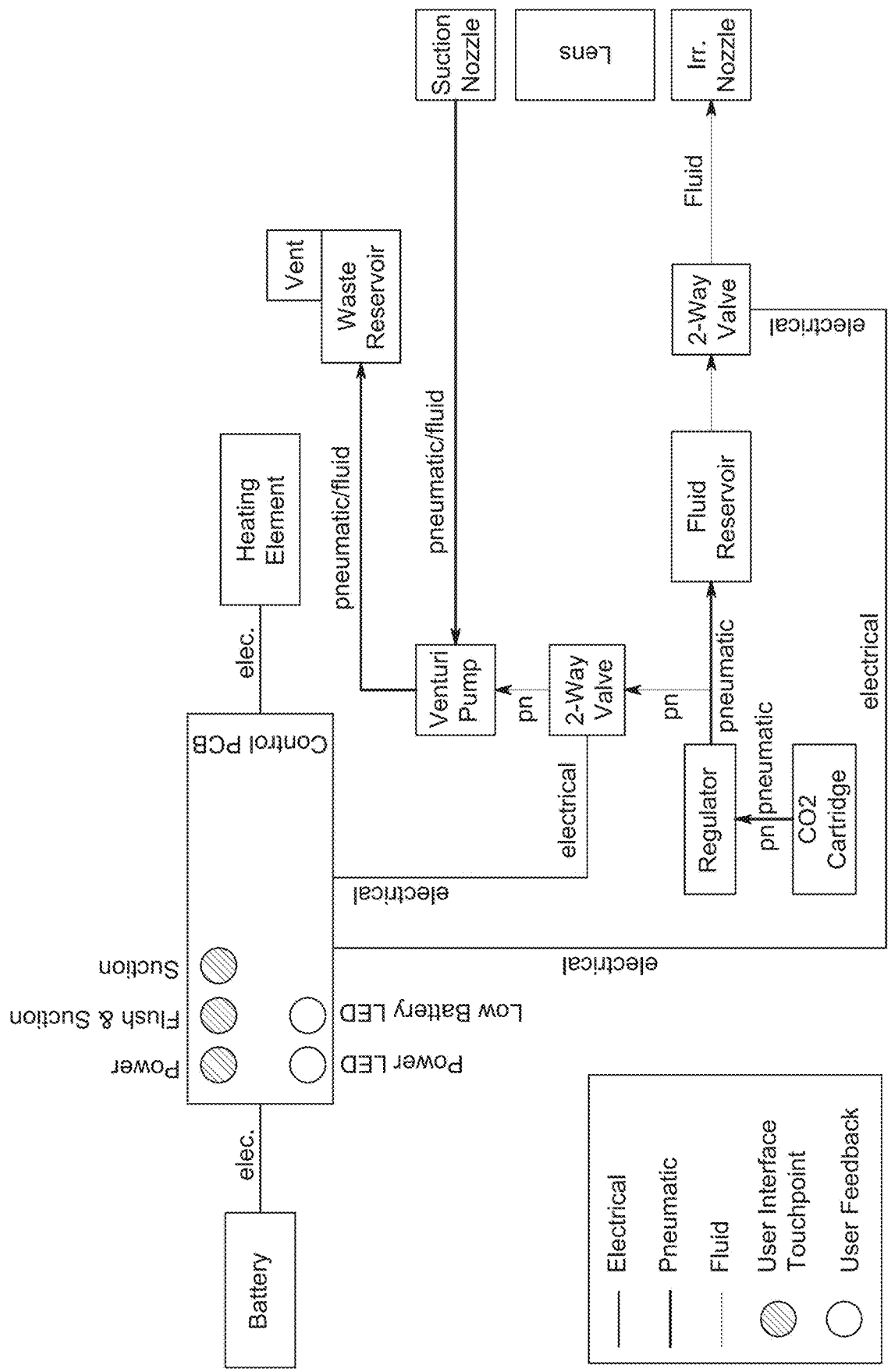
FIG. 22a illustrates a schematic for an embodiment of a cleaning device using vacuum drying.
Figure 22B:
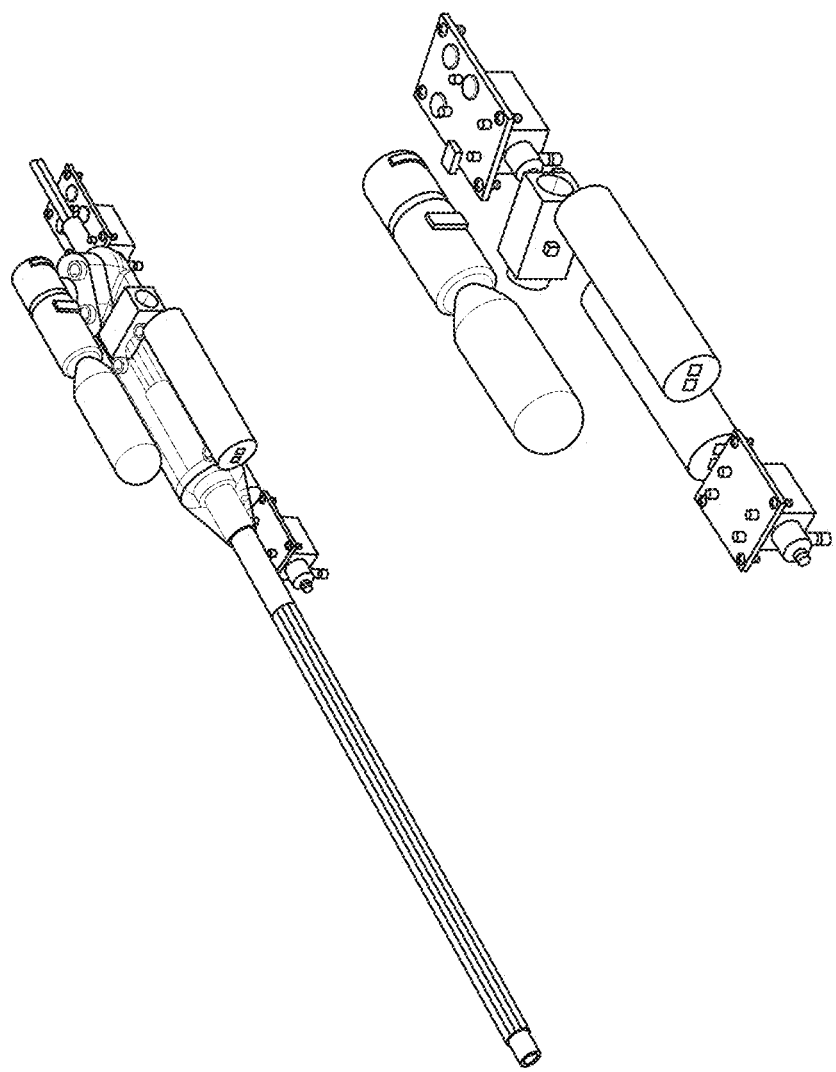
FIG. 22b illustrates a layout for an embodiment of a cleaning device using vacuum drying.

FIGS. 22a and 22b illustrate an electrical control schematic and layout for an embodiment of a cleaning device using vacuum drying. In the embodiment shown, electronically controlled valves are used to enable cycle control. The fluid reservoir is relatively constantly pressurized. A downstream valve is provided and may be disposable.

Figure 23A:
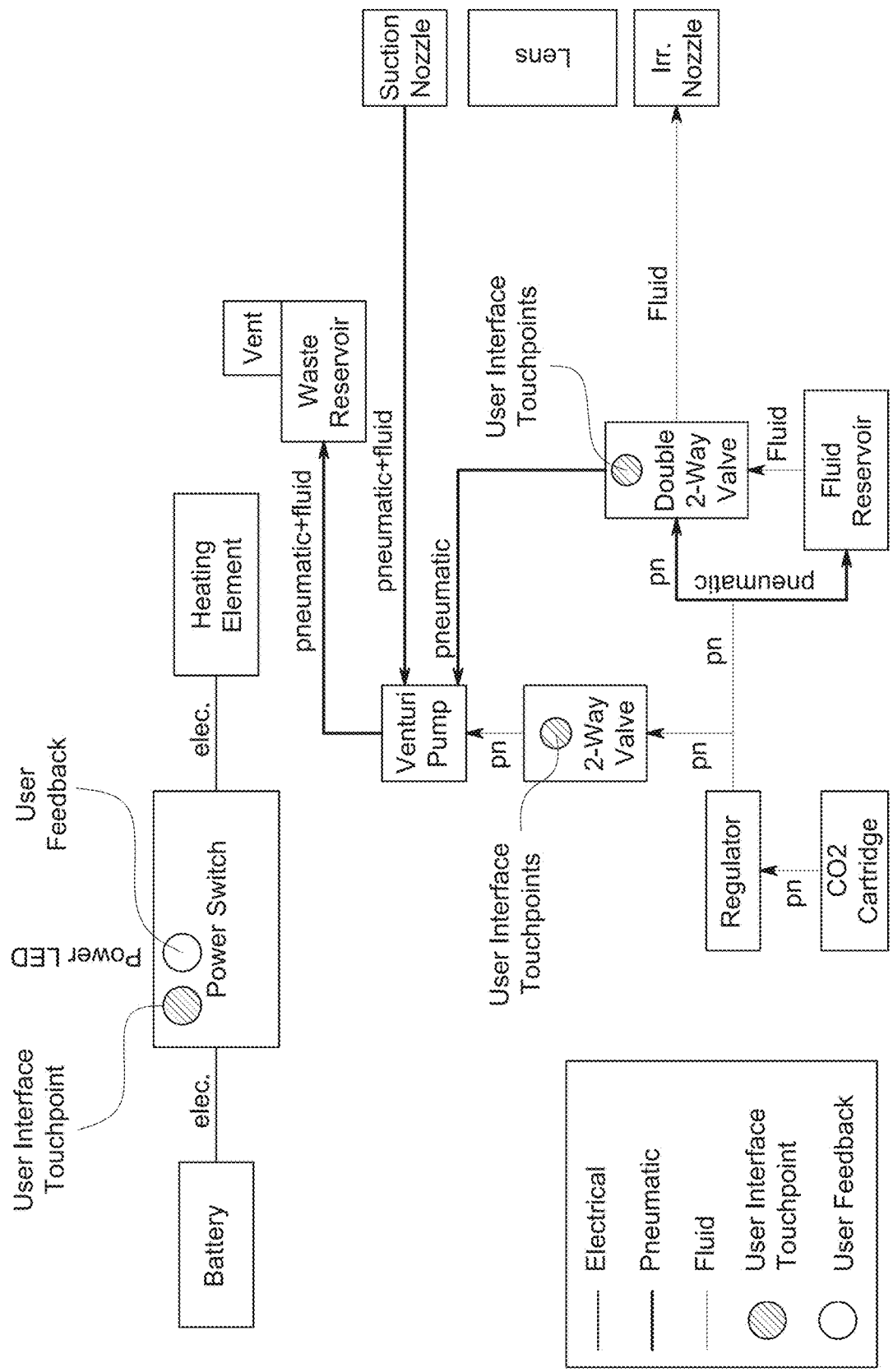
FIG. 23a illustrates a schematic for a cleaning device using jet drying, in accordance with another embodiment.
Figure 23B:
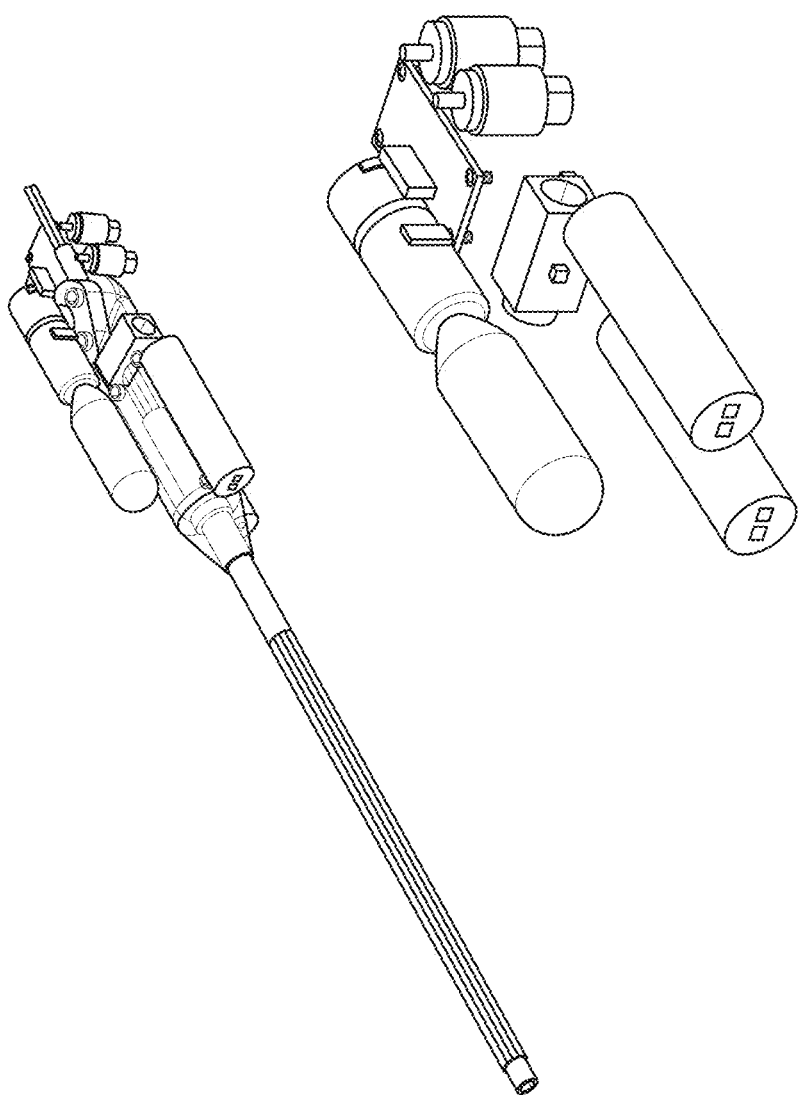
FIG. 23b illustrates a layout a cleaning device using jet drying, in accordance with another embodiment.

FIGS. 23a and 23b illustrate a mechanical control schematic and layout for another embodiment of a cleaning device using vacuum drying. In the embodiment shown, mechanically controlled valves are used to operate the device. The fluid reservoir is relatively constantly pressurized. A downstream valve is provided and may be disposable.

Figure 24A:
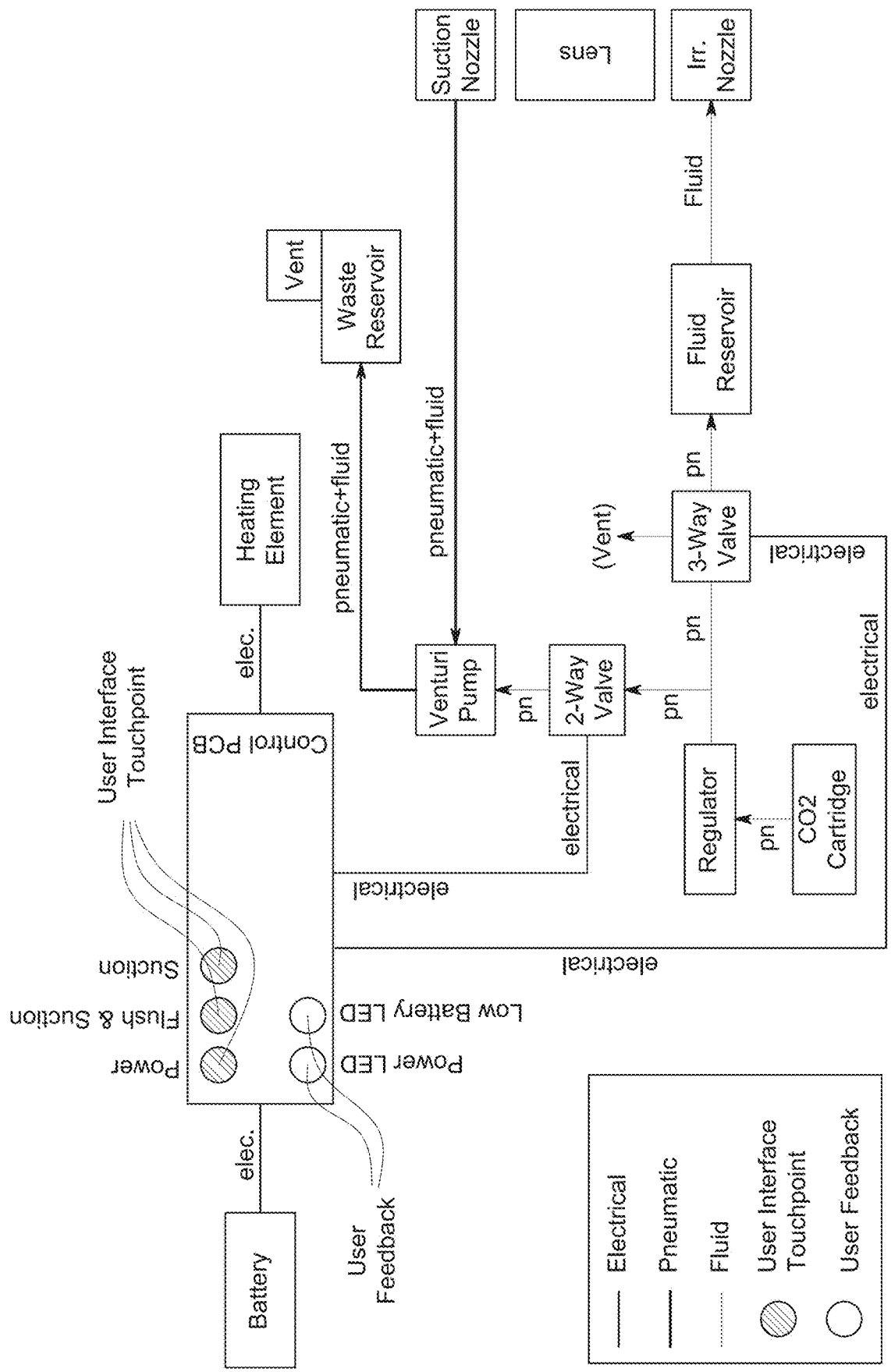
FIG. 24a illustrates a schematic for a cleaning device using vacuum drying, in accordance with another embodiment.
Figure 24B:
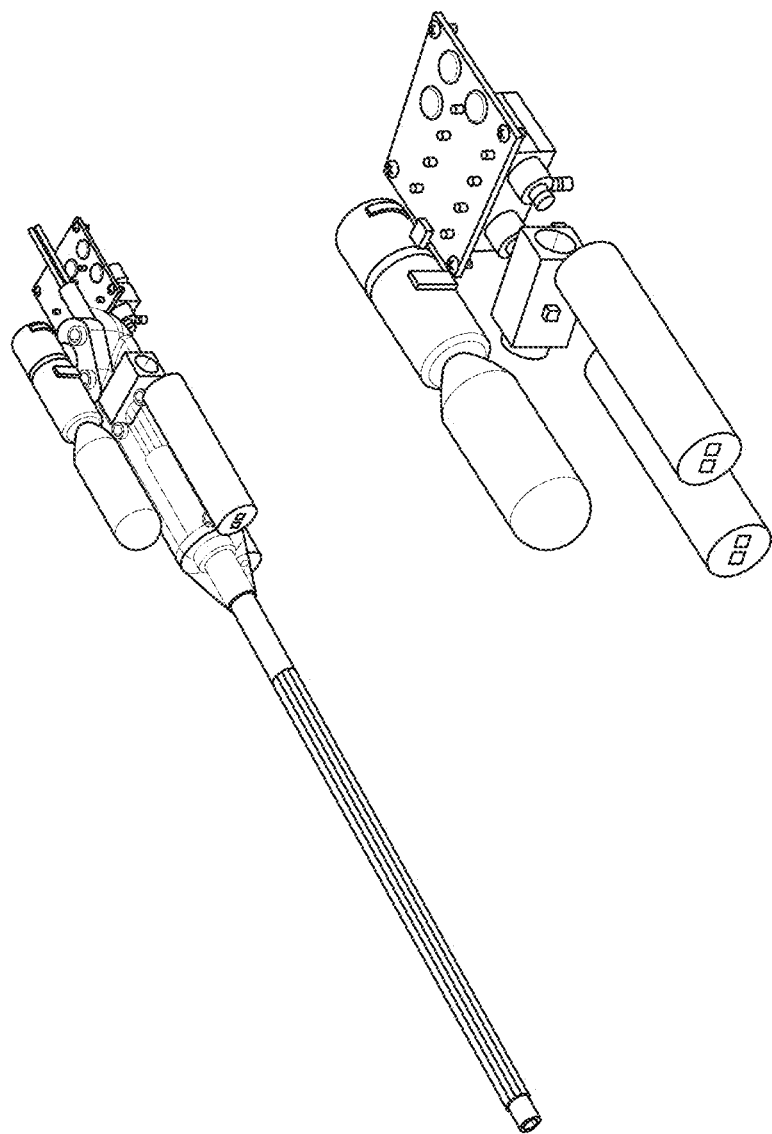
FIG. 24b illustrates a layout a cleaning device using vacuum drying, in accordance with another embodiment.

FIGS. 24a and 24b illustrate an electrical control schematic and layout for yet another embodiment of a cleaning device using vacuum drying. In the embodiment shown, electronically controlled valves are used to enable cycle control. The fluid reservoir is vented. An upstream valve is provided and may be reusable.

Figure 25A:
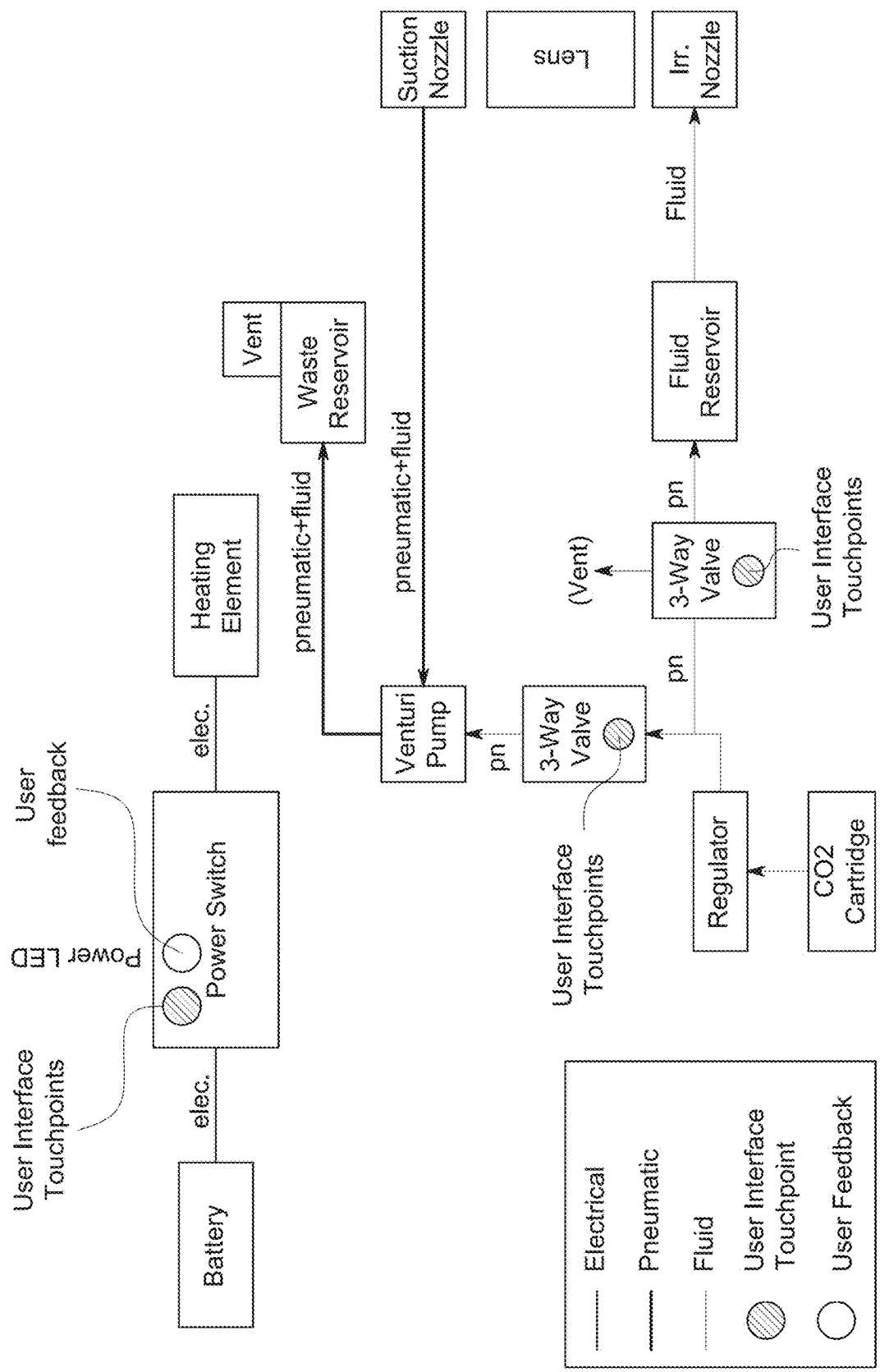
FIG. 25a illustrates a schematic for a cleaning device using vacuum drying, in accordance with a further embodiment.
Figure 25B:
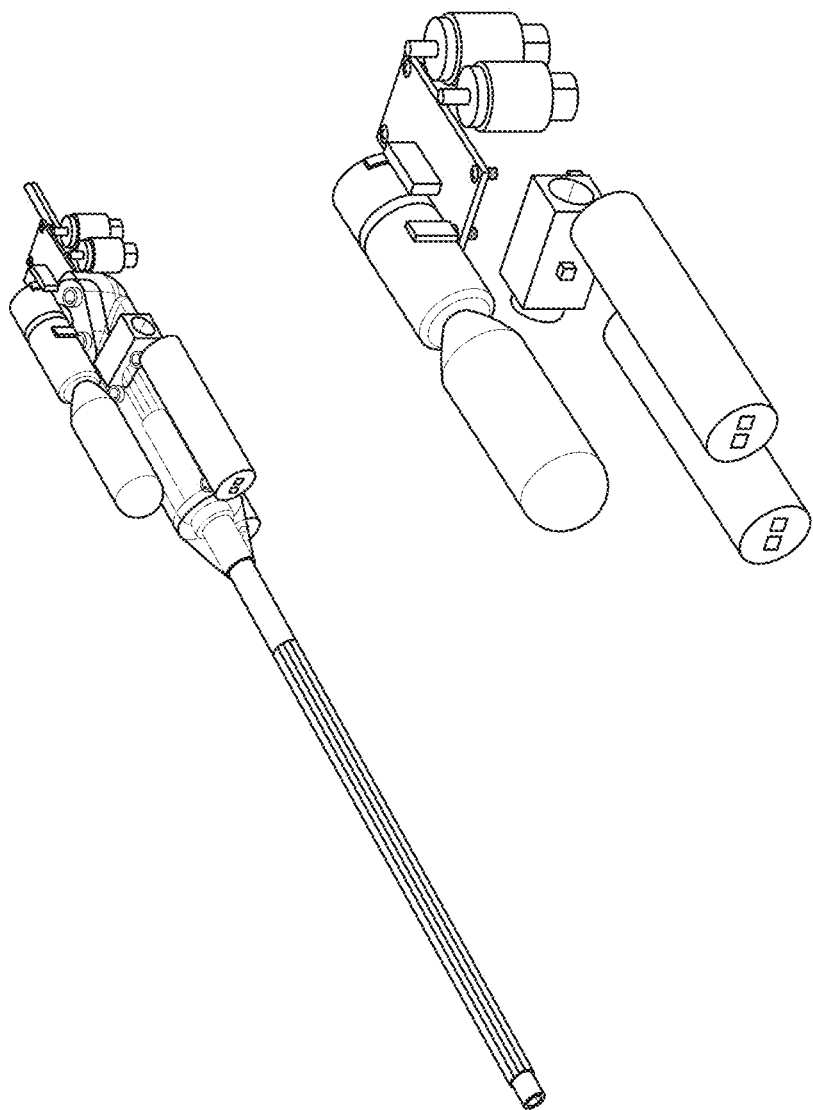
FIG. 25b illustrates a layout a cleaning device using vacuum drying, in accordance with a further embodiment.

FIGS. 25a and 25b illustrate a mechanical control schematic and layout for a further embodiment of a cleaning device using vacuum drying. In the embodiment shown, mechanically controlled valves are used to operate the device. The fluid reservoir is vented. An upstream valve is provided and may be reusable.

Figure 26A:
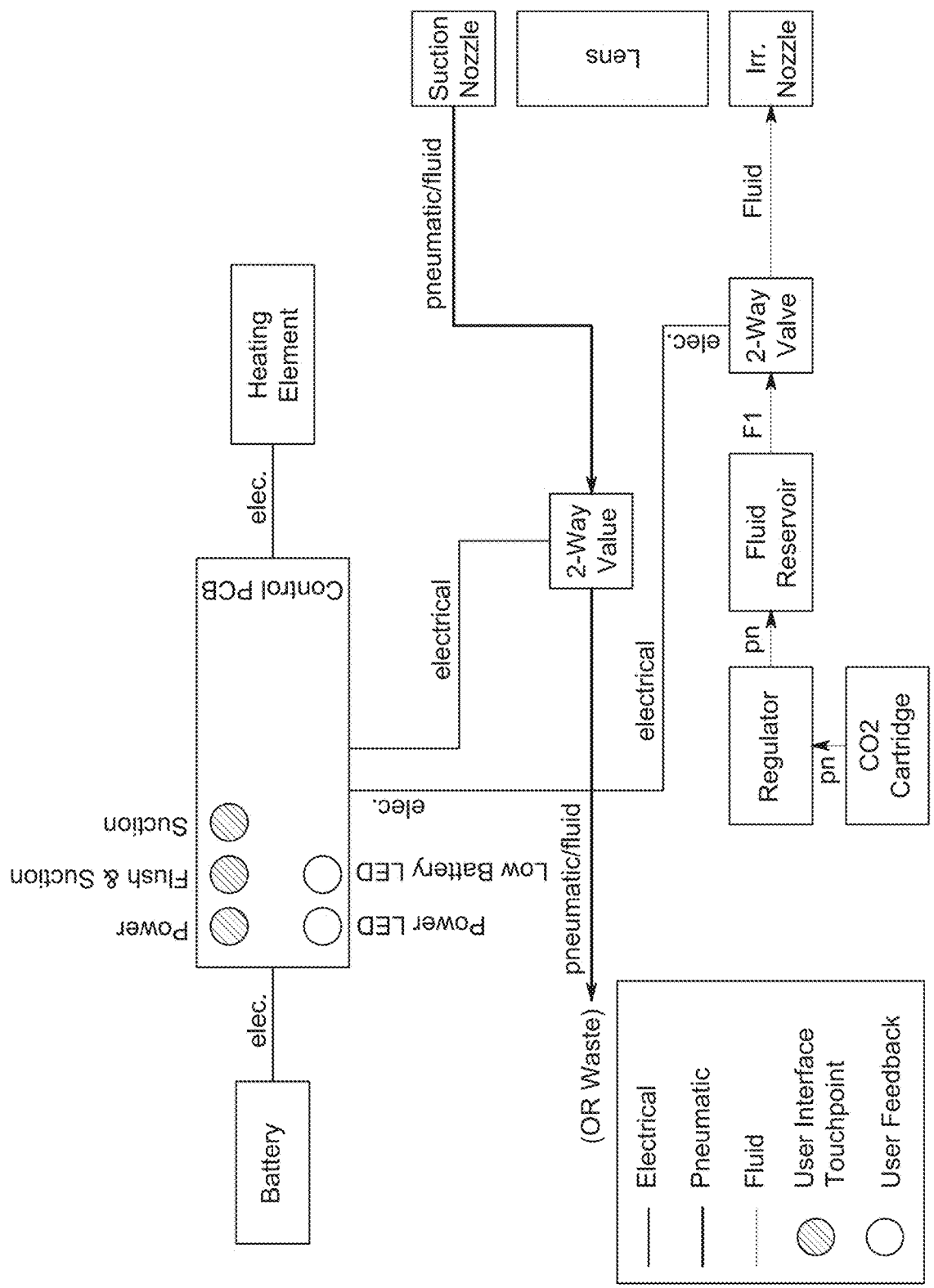
FIG. 26a illustrates a schematic for a cleaning device using operating supplied suction, in accordance with one embodiment.
Figure 26B:
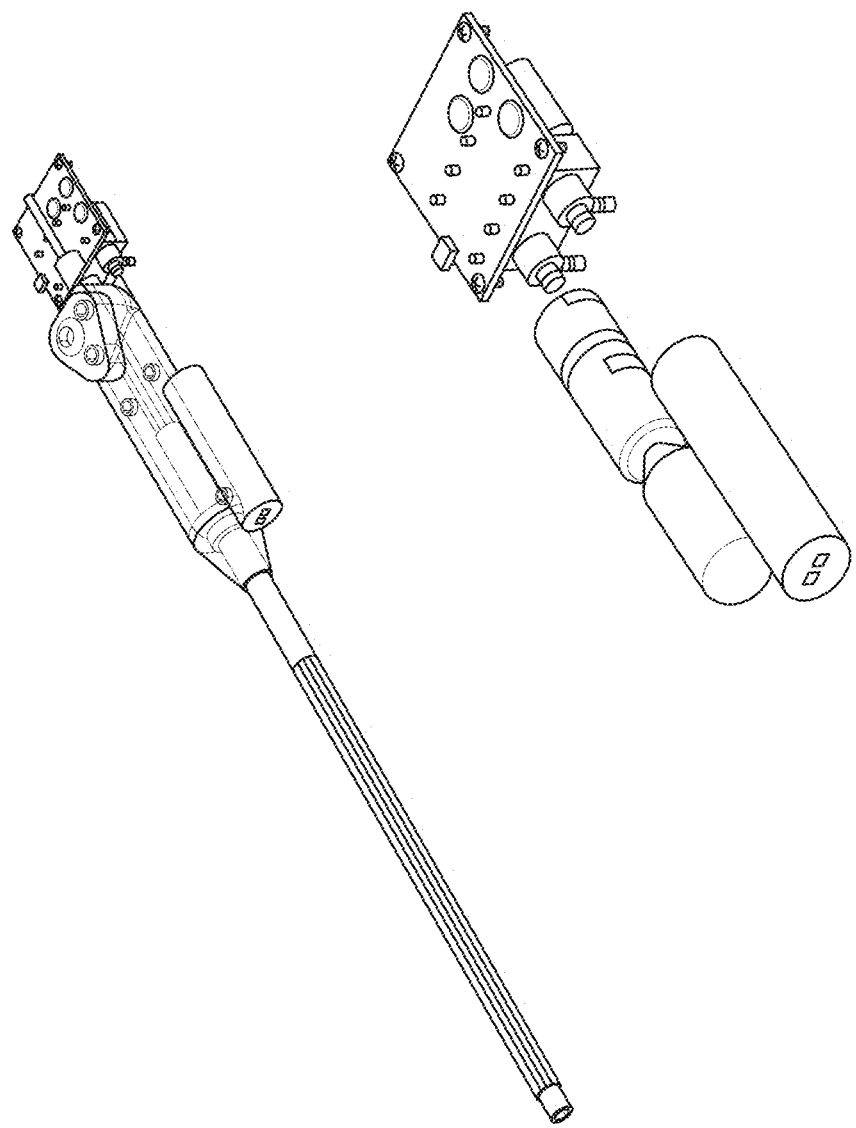
FIG. 26b illustrates a layout a cleaning device using operating supplied suction, in accordance with one embodiment.

FIGS. 26a and 26b illustrate a schematic and layout for an embodiment of a cleaning device using operating room supplied suction. In such an embodiment, no venturi valve, waste reservoir, or vent is used. The $CO_2$ cartridge may have a reduced size compared to a $CO_2$ cartridge for a cleaning device using suction but with suction being driven by the $CO_2$ device. In the embodiment shown, electronically controlled valves are used and enable cycle control. The fluid reservoir is relatively constantly pressurized. A downstream valve is provided and may be disposable.

Figure 27A:
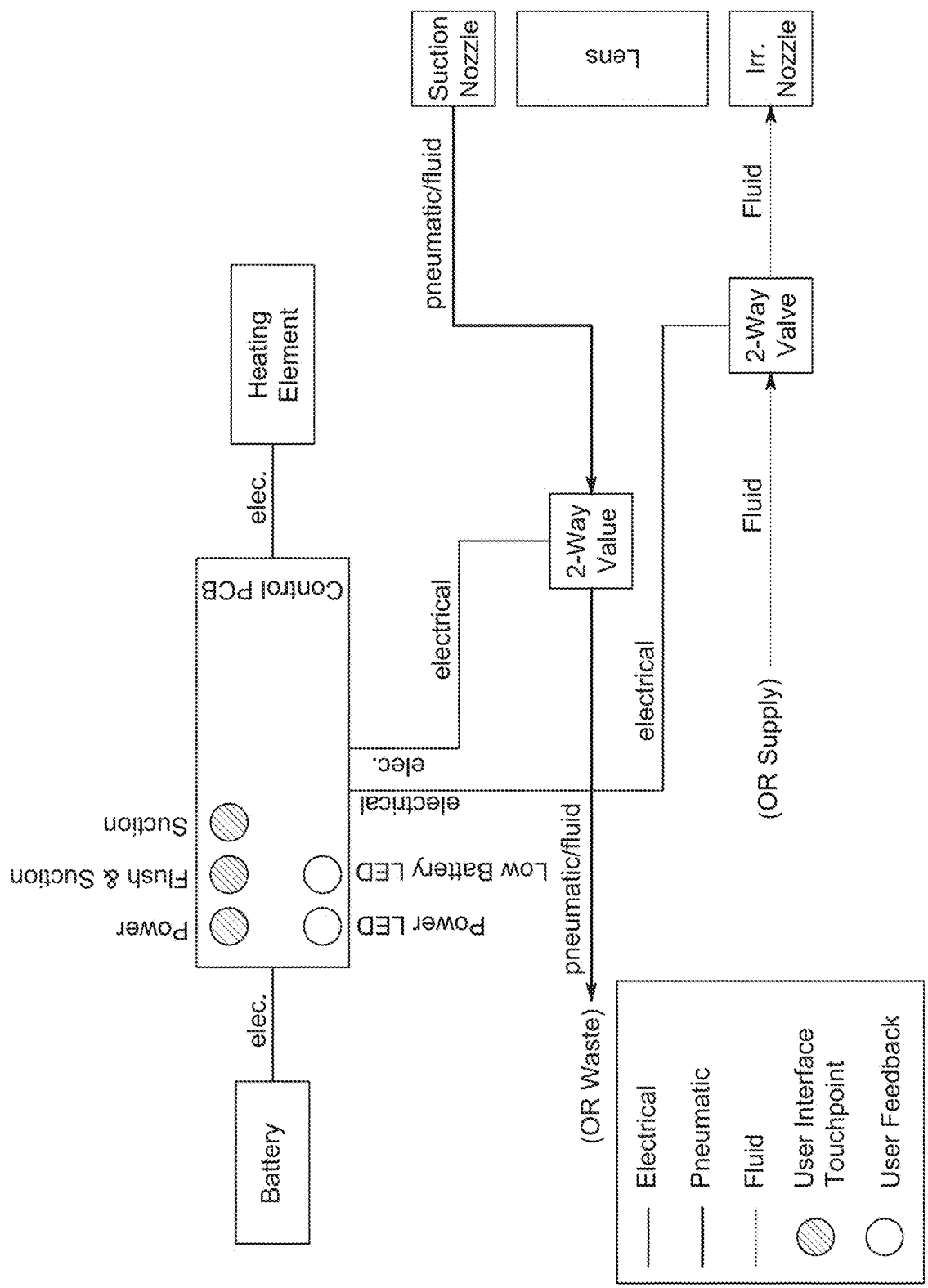
FIG. 27a illustrates a schematic for a cleaning device using operating supplied suction, in accordance with another embodiment.
Figure 27B:
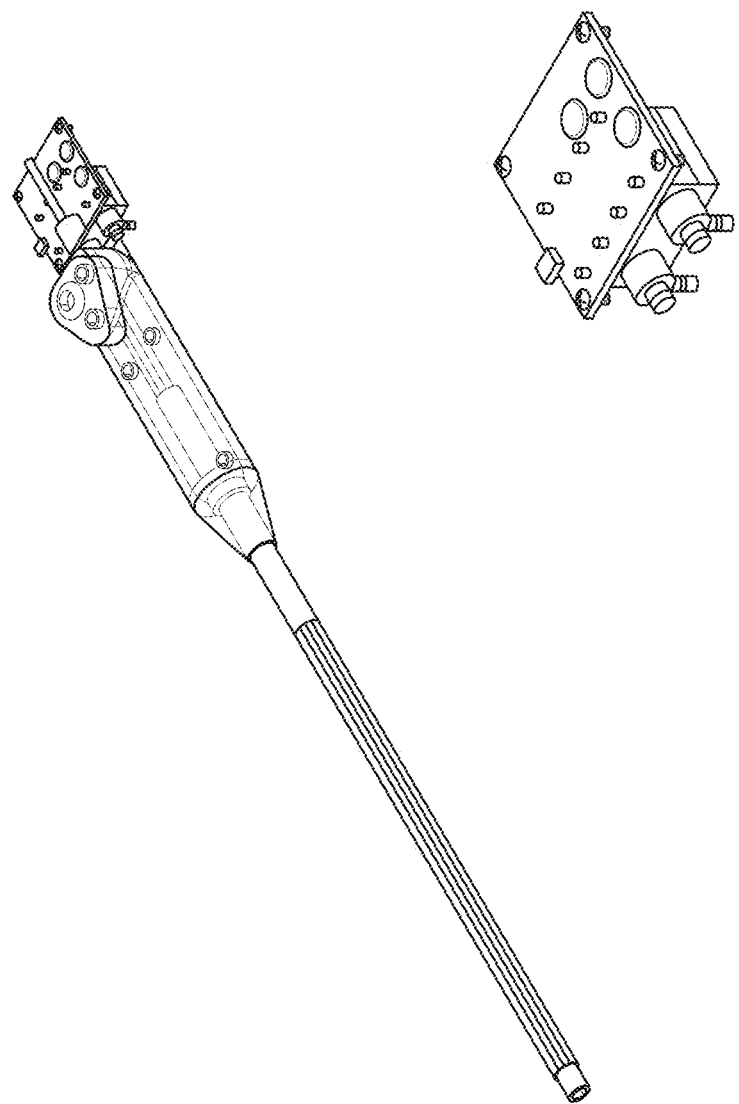
FIG. 27b illustrates a layout a cleaning device using operating supplied suction, in accordance with another embodiment.

FIGS. 27a and 27b illustrate a schematic and layout for a further embodiment of a cleaning device using operating room supplied suction. In such an embodiment, no venturi valve, waste reservoir, or vent is used. The $CO_2$ cartridge may have a reduced size compared to a $CO_2$ cartridge for a cleaning device using suction but with suction being driven by the $CO_2$ device. In the embodiment shown, electronically controlled valves are used and enable cycle control. The fluid reservoir is relatively constantly pressurized. A downstream valve is provided and may be disposable.

Figure 28A:
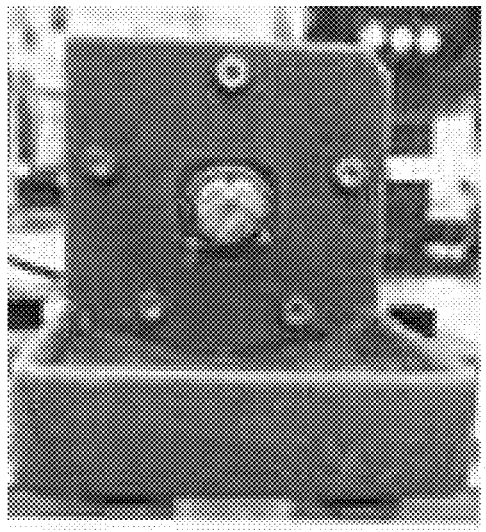
FIG. 28a illustrates a soiled scope.
Figure 28B:
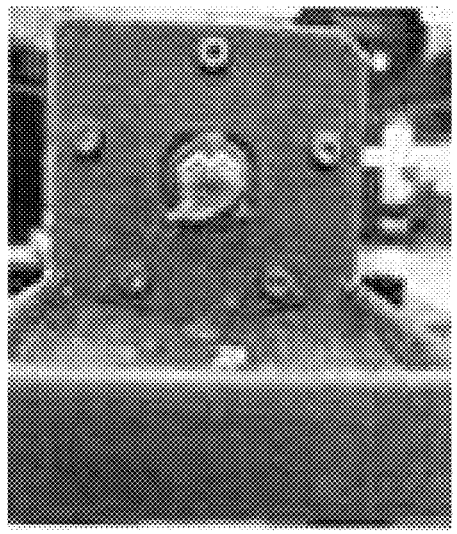
FIG. 28b illustrates the scope of FIG. 28a after an initial wash at 5 psi irrigation and 40 psi jet-dry using an embodiment of a cleaning device as described herein.
Figure 29A:
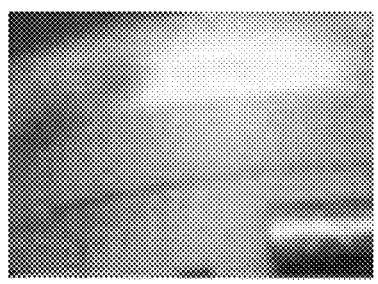
FIG. 29a illustrates a pre-soiled scope.
Figure 29B:
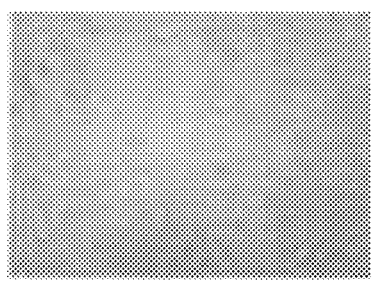
FIG. 29b illustrates the scope of FIG. 29a in a soiled condition.
Figure 29C:
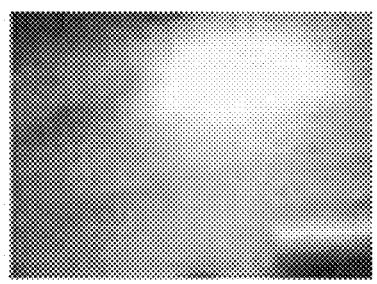
FIG. 29c illustrates the scope of FIG. 29c after cleaning using an embodiment of a cleaning device as described herein.

FIGS. 28a and 28b illustrate a soiled scope and the soiled scope after an initial wash at 5 psi irrigation and 40 psi jet-dry using a cleaning device as described herein. FIGS. 29a-29c illustrate a pre-soiled scope, a soiled scope, and a post cleaning scope wherein the soiled scope was cleaned using a cleaning device as described herein.

In general, the following parameters may be considered in selecting combinations from the above options:
Nozzle geometry for irrigation channel;
Nozzle geometry for jet-dry channel;
Heating (power use, heater geometry, etc.);
Irrigation time for a cleaning cycle;
Jet-dry time for a cleaning cycle;
Liquid volume for a cleaning cycle; and
$CO_2$ volume for a cleaning cycle.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein, the phrase "at least one of [X] and [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A cleaning device system for use with a surgical device having a shaft and a lens at a distal end of the shaft, the cleaning device system comprising:
   a cleaning device comprising:
      a sheath for fitting over the shaft of the surgical device, the sheath having an irrigation channel, a drying channel, and a heating channel, wherein the heating channel is disposed proximate the irrigation channel; and
      a nozzle coupled to a distal end of the sheath, the nozzle having an irrigation port and a drying port, the irrigation channel terminating at the irrigation port and the drying channel terminating at the drying port; and
   a module housing an irrigation fluid reservoir, a gas canister, and a power source;
   wherein a first fluid is dispensed from the irrigation fluid reservoir in the module through the irrigation channel in the sheath and out the irrigation port in the nozzle and a second fluid is dispensed from the gas canister in the module through the drying channel in the shaft and out the drying port in the nozzle; and
   a control pad having a first button and a second button, wherein the first button runs a cleaning cycle including dispensing the first fluid and the second button runs a drying cycle including dispensing the second fluid.

2. The cleaning device system of claim 1, wherein the irrigation fluid reservoir is refillable during a surgical procedure.

3. The cleaning device system of claim 1, wherein the gas canister is replaceable during a surgical procedure.

4. The cleaning device system of claim 1, wherein the irrigation fluid reservoir has a volume sufficient for ten cleanings without refilling.

5. The cleaning device system of claim 1, wherein the irrigation port and the drying port are provided on opposite sides of the nozzle.

6. The cleaning device system of claim 1, wherein the irrigation port and the drying port are provided on a same side of the nozzle.

7. The cleaning device system of claim 1, wherein the cleaning cycle further comprises dispensing the second fluid.

8. The cleaning device system of claim 1, wherein the first fluid is saline and the second fluid is carbon dioxide gas.

9. The cleaning device system of claim 1, wherein the nozzle is configured to direct the first fluid across the lens.

10. The cleaning device system of claim 1, wherein the sheath and the nozzle are disposable.

11. The cleaning device system of claim 1, further comprising an irrigation tube running from the irrigation fluid reservoir to the irrigation channel and a drying tube running from the $CO_2$ canister to the drying tube.

12. The cleaning device system of claim 1, further comprising a heating element disposed in the heating channel.

13. A cleaning device system for use with a surgical device having a shaft and a lens at a distal end of the shaft, the cleaning device system comprising:
a cleaning device comprising:
a sheath for fitting over the shaft of the surgical device, the sheath having an irrigation channel, a drying channel, and a heating channel, wherein the heating channel is disposed proximate the irrigation channel;
a nozzle coupled to a distal end of the sheath, the nozzle having an irrigation port and a drying port, the irrigation channel terminating at the irrigation port and the drying channel terminating at the drying port; and
a module housing an irrigation fluid reservoir, a $CO_2$ canister, and a power source, wherein the irrigation fluid reservoir has a volume sufficient for at least ten cleanings without refilling;
wherein saline is dispensed from the irrigation fluid reservoir in the module through the irrigation channel in the sheath and out the irrigation port in the nozzle and $CO_2$ gas is dispensed from the gas canister in the module through the drying channel in the shaft and out the drying port in the nozzle;
wherein the saline is heated to a temperature of at least 104° F. in the irrigation channel; and
a control pad having a first button and a second button, wherein the first button runs a cleaning cycle comprising dispensing the saline and dispensing the $CO_2$ and the second button runs a supplemental drying cycle comprising dispensing the $CO_2$.

* * * * *